(12) United States Patent
Maurer et al.

(10) Patent No.: US 11,107,565 B2
(45) Date of Patent: Aug. 31, 2021

(54) SYSTEMS AND METHODS FOR PROVIDING PROFESSIONAL TREATMENT GUIDANCE FOR DIABETES PATIENTS

(71) Applicant: TIGAR Health, Inc., Moraga, CA (US)

(72) Inventors: Robert Maurer, Moraga, CA (US); Barry Ginsberg, Moraga, CA (US)

(73) Assignee: TIGAR HEALTH, INC., Moraga, CA (US)

(*) Notice: Subject to any disclaimer, the term of this patent is extended or adjusted under 35 U.S.C. 154(b) by 122 days.

(21) Appl. No.: 16/179,429

(22) Filed: Nov. 2, 2018

(65) Prior Publication Data

US 2019/0131007 A1    May 2, 2019

Related U.S. Application Data

(60) Provisional application No. 62/580,889, filed on Nov. 2, 2017.

(51) Int. Cl.

| | |
|---|---|
| *G16H 15/00* | (2018.01) |
| *G16H 10/60* | (2018.01) |
| *G16B 40/00* | (2019.01) |
| *A61B 5/00* | (2006.01) |
| *G16H 50/20* | (2018.01) |
| *G16H 20/10* | (2018.01) |

(52) U.S. Cl.
CPC ........... *G16H 15/00* (2018.01); *A61B 5/4866* (2013.01); *G16B 40/00* (2019.02); *G16H 10/60* (2018.01); *G16H 20/10* (2018.01); *G16H 50/20* (2018.01)

(58) Field of Classification Search
CPC ........ G16H 15/00; G16H 10/60; G16H 20/10; G16H 50/20; A61B 5/4866; G16B 40/00
See application file for complete search history.

(56) References Cited

U.S. PATENT DOCUMENTS

| | | | |
|---|---|---|---|
| 6,731,978 B2 * | 5/2004 | Olson | A61B 5/042 607/14 |
| 2006/0031094 A1 * | 2/2006 | Cohen | G16H 20/17 705/2 |

(Continued)

OTHER PUBLICATIONS

Classification and Diagnosis of Diabetes, 39(Supplement 1) American Diabetes Association S13-S22 (Jan. 2016) (Year: 2016).*

(Continued)

*Primary Examiner* — Evangeline Barr
*Assistant Examiner* — Jordan L Jackson

(57) ABSTRACT

Systems and methods are provided for providing diabetes patient treatment guidance for a patient in which a biochemical data set is obtained. The biochemical data set comprises test results from a single blood draw of the patient including at least three measurements selected from the set: a high-sensitivity c-reactive protein test, an adiponectin level test, an intact proinsulin level test, an insulin level test, a C-peptide test, a HbA1c test, and an eGFR level test. A demographic data set for the patient is also obtained that comprises the patient's gender and diabetes stage. The biochemical data set and demographic data set is run against one or more rules to determine a first patient therapy pattern. Then, a report is prepared based on an identity of the first therapy patient pattern. The report sets priorities among intervention classes for the patient based on the identity of the first patient pattern.

15 Claims, 29 Drawing Sheets

(56) References Cited

U.S. PATENT DOCUMENTS

| | | |
|---|---|---|
| 2006/0089854 A1 | 4/2006 | Holland et al. |
| 2008/0097792 A1 | 4/2008 | Marge |
| 2015/0356252 A1 | 12/2015 | Beker |
| 2018/0024143 A1* | 1/2018 | McKenna .............. G16H 50/50 506/9 |

OTHER PUBLICATIONS

Wilson et. al., Prediction of Incident Diabetes Mellitus in Middle-aged Adults, The Framingham Offspring Study (Year: 2007).*

• Khodabandeloo et al., Molecular and cellular mechanisms linking inflammation to insulin resistance and /3-cell dysfunction, 167(1) Translational Research 228-256 (Jan. 2016) (Year: 2016).*

* cited by examiner

Ordered Items
CBC With Differential/Platelet; Comp. Metabolic Panel (14); LP+Non HDL Cholesterol; Hemoglobin A1c; Adiponectin; C-Peptide,
Serum; C-Reactive Protein; Cardiac; Proinsulin; Insulin; Venipuncture

| TESTS | RESULT | FLAG | UNITS | REFERENCE INTERVAL | LAB |
|---|---|---|---|---|---|
| CBC With Differential/Platelet | | | | | |
| WBC | 5.5 | | x10E3/uL | 3.4 - 10.8 | 01 |
| RBC | 5.14 | | x10E6/uL | 4.14 - 5.80 | 01 |
| Hemoglobin | 16.2 | | g/dL | 13.0 - 17.7 | 01 |
| Hematocrit | 46.5 | | % | 37.5 - 51.0 | 01 |
| MCV | 91 | | fL | 79 - 97 | 01 |
| MCH | 31.5 | | pg | 26.6 - 33.0 | 01 |
| MCHC | 34.8 | | g/dL | 31.5 - 35.7 | 01 |
| RDW | 13.2 | | % | 12.3 - 15.4 | 01 |
| Platelets | 197 | | x10E3/uL | 150 - 379 | 01 |
| Neutrophils | 50 | | % | Not Estab. | 01 |
| Lymphs | 43 | | % | Not Estab. | 01 |
| Monocytes | 5 | | % | Not Estab. | 01 |
| Eos | 3 | | % | Not Estab. | 01 |
| Basos | 0 | | % | Not Estab. | 01 |
| Neutrophils (Absolute) | 2.7 | | x10E3/uL | 1.4 - 7.0 | 01 |
| Lymphs (Absolute) | 2.4 | | x10E3/uL | 0.7 - 3.1 | 01 |
| Monocytes(Absolute) | 0.3 | | x10E3/uL | 0.1 - 0.9 | 01 |
| Eos (Absolute) | 0.1 | | x10E3/uL | 0.0 - 0.4 | 01 |
| Baso (Absolute) | 0.0 | | x10E3/uL | 0.0 - 0.2 | 01 |
| Immature Granulocytes | 0 | | % | Not Estab. | 01 |
| Immature Grans (Abs) | 0.0 | | x10E3/uL | 0.0 - 0.1 | 01 |
| Comp. Metabolic Panel (14) | | | | | |
| Glucose | 95 | | mg/dL | 65 - 99 | 01 |
| BUN | 21 | | mg/dL | 6 - 24 | 01 |
| Creatinine | 1.00 | | mg/dL | 0.76 - 1.27 | 01 |
| eGFR If NonAfricn Am | 86 | | mL/min/1.73 | >59 | |
| eGFR If Africn Am | 100 | | mL/min/1.73 | >59 | |
| BUN/Creatinine Ratio | 21 | High | | 9 - 20 | |

Fig. 5B

| TESTS | RESULT | FLAG | UNITS | REFERENCE INTERVAL | LAB |
|---|---|---|---|---|---|
| Sodium | 145 | High | mmol/L | 134 - 144 | 01 |
| Potassium | 5.0 | | mmol/L | 3.5 - 5.2 | 01 |
| Chloride | 104 | | mmol/L | 96 - 106 | 01 |
| Carbon Dioxide, Total | 26 | | mmol/L | 20 - 29 | 01 |
| | Please note reference interval change | | | | |
| Calcium | 9.8 | | mg/dL | 8.7 - 10.2 | 01 |
| Protein, Total | 7.0 | | g/dL | 6.0 - 8.5 | 01 |
| Albumin | 4.6 | | g/dL | 3.5 - 5.5 | 01 |
| Globulin, Total | 2.4 | | g/dL | 1.5 - 4.5 | |
| A/G Ratio | 1.9 | | | 1.2 - 2.2 | |
| Bilirubin, Total | 0.6 | | mg/dL | 0.0 - 1.2 | 01 |
| Alkaline Phosphatase | 36 | Low | IU/L | 39 - 117 | 01 |
| AST (SGOT) | 28 | | IU/L | 0 - 40 | 01 |
| ALT (SGPT) | 32 | | IU/L | 0 - 44 | 01 |
| LP+Non HDL Cholesterol | | | | | |
| Cholesterol, Total | 167 | | mg/dL | 100 - 199 | 01 |
| Triglycerides | 149 | | mg/dL | 0 - 149 | 01 |
| HDL Cholesterol | 36 | Low | mg/dL | >39 | 01 |
| VLDL Cholesterol Cal | 30 | | mg/dL | 5 - 40 | |
| LDL Cholesterol Calc | 101 | High | mg/dL | 0 - 99 | 01 |
| T. Chol/HDL Ratio | 4.6 | | ratio | 0.0 - 5.0 | |
| Please Note: | | | | T. Chol/HDL Ratio | |
| | | | | Men  Women | |
| | | | | 1/2 Avg.Risk  3.4  3.3 | |
| | | | | Avg.Risk  5.0  4.4 | |
| | | | | 2X Avg.Risk  9.6  7.1 | |
| | | | | 3X Avg.Risk  23.4  11.0 | |
| Non-HDL Cholesterol | 131 | High | mg/dL | 0 - 129 | 01 |

Fig. 5C

| pQL Drugs | Column 1 | Column 2 | Column 3 | Proposal 1 | Proposal 2 BHO Suggestions |
|---|---|---|---|---|---|
| Pattern #1 | Insulin Resistance: Severe | Beta-cell Stress: Significant | Cardiovascular: High | Drug Order: M, T, S, D, G, I | M, S, G, D, I, T, F, I |
| Pattern #2 | Insulin Resistance: Severe | Beta-cell Stress: Significant | Cardiovascular: Moderate | Drug Order: M, T, S, D, G, I | M, S, G, D, T, F, I |
| Pattern #3 | Insulin Resistance: Severe | Beta-cell Stress: Significant | Cardiovascular: Normal | Drug Order: M, T, S, D, G, I | M, S, G, T, D, F, I |
| Pattern #4 | Insulin Resistance: Severe | Beta-cell Stress: Great | Cardiovascular: High | Drug Order: M, T, S, D, G, I | M, S, G, D, I, T, F, I |
| Pattern #5 | Insulin Resistance: Severe | Beta-cell Stress: Great | Cardiovascular: Moderate | Drug Order: M, T, S, D, G, I | M, S, G, D, T, F, I |
| Pattern #6 | Insulin Resistance: Severe | Beta-cell Stress: Great | Cardiovascular: Normal | Drug Order: M, T, S, D, G, I | M, S, G, T, D, F, I |
| Pattern #7 | Insulin Resistance: Severe | Beta-cell Stress: Moderate | Cardiovascular: High | Drug Order: T, M, S, D, G, I | M, S, G, D, I, T, F, I |
| Pattern #8 | Insulin Resistance: Severe | Beta-cell Stress: Moderate | Cardiovascular: Moderate | Drug Order: T, M, S, D, G, I | M, S, G, D, T, F, I |
| Pattern #9 | Insulin Resistance: Severe | Beta-cell Stress: Moderate | Cardiovascular: Normal | Drug Order: T, M, S, D, G, I | M, S, G, T, D, F, I |
| Pattern #10 | Insulin Resistance: Severe | Beta-cell Stress: Normal | Cardiovascular: High | Drug Order: T, M, S, D, G, I | M, S, G, D, I, T, F, I |
| Pattern #11 | Insulin Resistance: Severe | Beta-cell Stress: Normal | Cardiovascular: Moderate | Drug Order: T, M, S, D, G, I | M, S, G, T, D, F, I |
| Pattern #12 | Insulin Resistance: Severe | Beta-cell Stress: Normal | Cardiovascular: Normal | Drug Order: T, M, S, D, G, I | M, S, G, T, D, F, I |

Test Result Interpretation

Moderately elevated hsCRP result indicates that attention should also focus on cardiovascular disease. Levels of hsCRP between 1 ug/ml to 3 ug/ml are associated with cardiovascular inflammation, developing atherosclerosis and moderately increased risk of major cardiovascular events [1][2].

High normal proinsulin, high insulin and high C-peptide levels indicate significant beta-cell stress despite therapy.

Moderately decreased adiponectin and the beta-cell marker pattern indicate that insulin resistance is developing. Insulin resistance is moderate [3][5].

Elevated HbA1c result indicates significantly impaired glucose control [21].

Low eGFR indicates significant renal function impairment.

Note: Comparative data for the TIGAR™ biomarkers other than HbA1c, in some cases, will demonstrate improvements much more quickly, and of much greater magnitude than HbA1c. Improvements seen in patient condition may be independent of glucose control [20].

Summary. Current Drug Recommendations. See "Current Drug Recommendations" Below

Preferred
1. Healthy eating and physical activity
2. Multiple drug therapy is indicated. Adjusting for renal impairment, choose among:
   a. metformin
   b. GLP-1 analogs
   c. SGLT-2 inhibitors
   d. TZDs
   e. DPP-4 inhibitors

Possible
1. Insulin

Not Recommended
1. Sulfonylureas
2. Glinides

Patient Current Condition

Fig. 10B

IR2Dx TIGAR™ REPORT

Patient PATIENT NAME   DOB: 09/16/1954   Requested by: CLINICIAN   Collected: 09/16/2016

Patient has continuing dysregulation despite diabetes therapy:
- Beta-cell stress is significant
- Insulin resistance is moderate
- Greater concern of developing insulin insufficiency Patient has moderately elevated risk hsCRP values:
- Cardiovascular & general inflammation risks associated with diabetes
- Probable developing atherosclerosis Patient has significant renal function impairment and significantly impaired glucose control:
- HbA1c levels are in the middle range associated with diabetes, with significantly impaired glucose control
- Renal function is impaired

Patient Goals

1. Improve response to diabetes therapy
2. Decrease significant beta-cell stress and reduce moderate insulin resistance
3. Manage potential cardiovascular disease (atherosclerosis)
4. Improve HbA1c level

Fig. 10C

Physician Course Of Action

1. Aggressive intervention suggested to lower HbA1c and improve metabolic control.
   - Therapy needs to be aimed primarily at addressing insulin insufficiency
   - May require a substitution and/or addition to the existing drug therapy
   - Consider addition of one or more low dose oral or subcutaneous diabetes medication while continuing existing therapy [3][5][18]
   - If patient is taking sulfonylureas or glinides, consider substituting another drug class
   - Continue to emphasize healthy eating and physical activity program
2. Cardiovascular management:
   - Further cardiovascular testing advised
   - Possible use of statins and rigorous blood pressure control
3. Adjust medications as needed for significant renal impairment Current Drug Recommendations IR2Dx has provided the following recommendations and interpretation based on the biomarker levels and demographic characteristics entered for this patient in the TIGAR™ Report. These recommendations allow simultaneous management of glucose control and underlying pathway function driving disease. We have provided suggestions for further assessment and monitoring of the patient outcomes. This TIGAR™ patient report is to be used by medical professionals, to supplement existing laboratory reporting systems for test results. Insulin resistance seems to be moderate, based upon the moderately decreased adiponectin and beta-cell marker pattern, and there is significant beta-cell stress and moderate cardiovascular inflammation despite therapy. Therapy needs to be aimed at reducing insulin resistance, and cardiovascular disease should receive attention. Dual drug therapy or more is indicated, with possible substitution for and/or addition to the existing drug therapy. Preferred 1. Institute or continue healthy eating and physical activity
2. Continue existing therapy, substituting or adding new drug classes

Fig. 10D c. Consider adding a TZD:
   1. Very effective against insulin resistance
   2. Has positive effect on cardiovascular risk factors
   3. Improves beta-cell and liver function
   4. Can have water retention and modest weight gain; taking drug at bedtime may reduce this [19][20]
   5. May worsen osteoporosis
   6. Inexpensive
d. Consider adding a DPP-4 inhibitor:
   1. Increases insulin secretion without hypoglycemia [26]
   2. Reduces glucose output
   3. Weight neutral
   4. Small manufacturer differences in certain cardiovascular event outcomes. (Detail in Advisory Notes)

Possible
1. Insulin therapy could be considered
   a. Addresses insulin insufficiency
   b. Relieves beta-cell stress
   c. Optimize basal insulin regimen, until fasting glucose levels are in the high normal range (115-125 mg/dl range)
   d. If goals cannot be reached without hypoglycemia, focus on reducing insulin resistance

Fig. 10F

IR2Dx

TIGAR™ REPORT

Patient PATIENT NAME    DOB: 09/16/1954    Prepared by: CLINICIAN    Collected: 09/16/2016

Not Recommended

1. Sulfonylureas are not optimal:
   a. Inexpensive
   b. Increase insulin secretion
   c. Do not address insulin resistance or cardiovascular disease
   d. May cause hypoglycemia, patients on sulfonylureas should monitor blood glucose, which increases the cost of monitoring treatment
   e. Use with caution in patients with cardiovascular disease and the elderly 2. Glinides:
   a. Do not address insulin resistance or cardiovascular disease

---

Recommended Adjustments for Renal Impairment & Chronic Kidney Disease

Up to 40% of patients with diabetes have impaired renal function. Choices of medications for patients with significant renal impairment, chronic kidney disease, or renal failure are limited, and frequently require adjustment of dose [13]. When the patient has renal function impairment or chronic kidney disease, drug class recommendations based on normal renal function should be adjusted as covered in this Recommended Adjustments for Renal Function Impairment & Chronic Kidney Disease section, with the degree of adjustment being commensurate with the degree of renal function impairment. Please see details by drug class below, check specific manufacturer product information as needed, and use as approved.

Fig. 10G

Possible:
1. Insulin:
   a. Kidney clearance of insulin is around half of total insulin clearance
   b. Directly affected by renal impairment
   c. Reduce dose as impairment increases
   d. Large reduction in clearance below eGFR of 20 mL/min
   e. Gastroparesis can occur in long standing diabetes (10+ years) and in renal failure
   f. Gastroparesis may hinder matching of food adsorption and insulin injections
   g. Can lead to erratic glucose regulation, complicated by hypoglycemia
2. Metformin:
   a. Primarily metabolized by the liver
   b. Incidence of lactic acidosis is increased with reduced eGFR
   c. Reduce dosage with reduced eGFR
   d. Do not use when serum creatinine is > 1.5 mg/dL for men, or > 1.4 mg/dL for women [21]
3. Thiazolidinediones:
   a. Metabolism of class is unaffected by renal impairment
   b. Water retention may be a problem [29]
4. GLP-1 analogs:
   a. Use in mild renal failure (eGFR 50-80 ml/min)
   b. Use with caution in moderate renal failure (eGFR 30-50 ml/min)
   c. Avoid in severe renal failure [14]
5. DPP-4 Inhibitors:
   a. May be used, but several require dosage adjustment based on the degree of renal failure [15]
   b. In hemodialysis cases, the dose should be administered immediately following dialysis

Fig. 10H

# IR2Dx

TIGAR™ REPORT

Patient PATIENT NAME  DOB: 09/10/1954  Requested by: CLINICIAN  Collected: 09/16/2016

6. SGLT-2 inhibitors:
   a. Mechanism of kidney clearance directly affected by renal impairment
   b. Not useful in severe renal failure
7. Sulfonylureas (if already in use and is continued):
   a. More patient in patients with renal impairment
   b. Should not be used in patients with severe renal failure

Retesting Protocol

- Retest using TIGAR™ biomarkers in three months to assess patient response
- Once the TIGAR™ biomarker levels improve, reduce testing frequency to six months

References

The specific references cited in this report can be located on the IR2Dx, Inc. website at http://www.ir2diagnostics.com/clinicians-health-professionals/tigar-report-reference-list/ (http://www.ir2diagnostics.com/clinicians-health-professionals/tigar-report-reference-list/) The list of references can be accessed in the IR2Dx TIGAR™ Report section (login required), under the heading List of References in TIGAR™ Report. Those abstracts and full reprints for the referenced publications, which are available by the publisher, can be viewed in this section: http://www.ir2diagnostics.com/research-product-development/publications/ (http://www.ir2diagnostics.com/research-product-development/publications/) A complete view of IR2Dx's Publications and Abstracts are also located on the IR2Dx website, under Research and Product Development, by title or year of publication. For additional assistance, please contact your laboratory test provider or IR2Dx, Inc. at www.ir2diagnostics.com/about-us/contact-us (http://www.ir2diagnostics.com/about-us/contact-us).

Fig. 10I

Advisory Notes And Limitations

The TICAP™ Report facilitates matching specific underlying pathway biochemistry, and thus the patient's appropriate personalized therapeutic target, to the best available drug based on the drug mechanism and effects [11,12] Breakpoints for HbA1c levels coincide with the American Association of Clinical Endocrinologists (AACE) Comprehensive Diabetes Management Algorithm, 2015 [21]. The clinical content of the TICAP™ Report is based on medical consensus. An expert advisory panel has been assembled by R2Dx for this purpose.

R2Dx results may be used to manage the treatment of certain pathway functions that underlie diabetes, cardiovascular disease, and other related diseases. These treatment suggestions are solely for professional use by a treating physician. The physician must determine the balance between glucose control, side effect risks, toleration of each drug, compliance issues, the effect on pathways underlying disease, medical history, and other factors in deciding what drugs, if any, to use for each patient.

Please refer to Physician's Desk Reference (PDR) or package insert available from the manufacturer for details on drug contraindications, side effect profile, black box warnings, if any, and potential drug combination incompatibilities based on all medications taken by this patient.

Please be advised that this TICAP™ Report, including its presented results, analysis and recommendations, are exemplary in nature and are intended solely as a supplementary aid to appropriately qualified health care professionals. In no circumstances is this TICAP™ Report or any aspect hereof intended as a substitute for a treating physician's independent judgment in light of all factors concerning an individual patient and should not in any circumstances be considered medical advice. Health care professionals are encouraged to use this TICAP™ Report in conjunction with, and not as a replacement for, their best clinical judgment.

Fig. 10J

TIGAR Health™
TIGAR™ REPORT
*Patient Summary*

The TIGAR™ Report is a new dimension on how to look at your health. It provides a personalized assessment on some of the key biochemistry markers to give a more robust understanding of your metabolic health.

--- hsCRP:
5.4 ug/ml
(High Sensitivity C-reactive protein)

You have very high level of inflammation - let's fix it! *Cardiovascular Disease*
- CRP is a reliable measure of general body inflammation.
- Low-grade chronic inflammation is related to Type 2 Diabetes and cardiovascular disease.
- Healthy eating and stress reduction can lower chronic inflammation.
- Sleep and exercise are known to decrease stress.

---

Adiponectin:
12 ug/ml

Your fat and muscle tissue are healthy - great! *Insulin Resistance*
- Adiponectin is a hormone produced by fat tissue.
- Low levels are correlated with high belly fat and diabetes.
- Weight loss, exercise, low saturated fatty acid diets (low-fat dairy, whole grains, poultry, fish, and nuts), and stress reduction reduce belly fat.

Fig. 10K

*Your beta cells are working way overtime!* *Insulin Sensitivity and Resistance*

- Beta cells in your pancreas produce proinsulin, which is then processed into insulin and C-peptide, two proteins which help control your metabolism.
- Insulin regulates blood glucose and effects the transport of glucose into cells.
- When a higher concentration of blood glucose is present, and cells resist glucose from entering, insulin resistance occurs
- In your case: Very high proinsulin, high insulin, and high C-peptide levels indicate great beta cell stress despite therapy.
- C-peptide has a role in kidney and nervous system function. It can be a useful measurement of your own insulin production, when taking insulin medications.
- Regular exercise stimulates cells to pull glucose out of the blood, reducing stress on beta cell production of insulin.

Insulin:
23 uIU/ml

Proinsulin:
20 pg/ml

C-peptide:
4 ng/ml

*You have great HbA1c - terrific!* *Blood Glucose Control*

- HbA1c is a measure of the average blood glucose levels over the last three months at the time of the blood sample collection.
- If overweight, weight loss is possibly the single most important action for lowering and stabilizing blood glucose levels.
- High blood sugar levels over time can damage your heart, blood vessels, kidneys, feet and eyes.

HbA1c:
5.9 %
(Hemoglobin A1c)

*Your kidneys are functioning well - great!* *Kidney Function*

- eGFR is an estimated measurement of kidney function.
- Kidney impairment and diabetes are related.
- Vegetables, fruits and low-sodium/low-fat foods are recommended to promote good kidney function.

eGFR:
81 ml/min
(Estimated Glomerular Filtration Rate)

Fig. 10L

SYSTEMS AND METHODS FOR PROVIDING PROFESSIONAL TREATMENT GUIDANCE FOR DIABETES PATIENTS

TECHNICAL FIELD

The present disclosure relates generally to systems and methods for providing Type 2 diabetes patient treatment guidance to professionals.

BACKGROUND

Type 2 diabetes mellitus is characterized by progressive disruption of normal physiologic insulin secretion and/or a significant cellular resistance to the action of insulin. The relative contribution of each of these factors in the resulting elevation of blood sugar can be important in selecting the proper diabetes therapy.

In healthy individuals, basal insulin secretion by pancreatic β-cells occurs continuously to maintain steady glucose levels for extended periods between meals. Also in healthy individuals, there is prandial secretion in which insulin is rapidly released in an initial first-phase spike in response to a meal, followed by prolonged insulin secretion that returns to basal levels after 2-3 hours.

Insulin is a hormone that binds to insulin receptors to lower blood glucose by facilitating cellular uptake of glucose, amino acids, and fatty acids into skeletal muscle and fat and by inhibiting the output of glucose from the liver. In normal healthy individuals, physiologic basal and prandial insulin secretions maintain euglycemia, which affects fasting plasma glucose and postprandial plasma glucose concentrations. Basal and prandial insulin secretion is impaired in Type 2 diabetes and early post-meal response is absent. To address these adverse events, subjects with Type 2 diabetes are provided with insulin medicament treatment regimens. The goal of these insulin medicament treatment regimens is to maintain a desired fasting blood glucose target level that will minimize estimated risk of hypo- and hyper-glycaemia.

There are a number of drugs available to treat diabetes in addition to insulin medicament. Which drugs are prescribed to a given subject depends on the stage of therapy of the subject, the subject's overall health, side effect risks, mode of administration, cost and formulary availability, as well as a number of physiological pathway considerations, typically assessed through measurements of one or more blood markers. Treatment regimens for each patient are ideally customized for the patient dependent upon these factors. However, conventional methods for devising a treatment regimen and sorting through the vast array of possible therapies that can be prescribed to a particular patient in need of treatment are presently unsatisfactory. In a typical situation, a doctor advising a particular patient would order two or three different tests to ascertain the condition of a diabetes patient. The metabolic pathophysiology is typically measured only in part, or much more often completely neglected. For instance, the doctor may order an A1C test and a renal function test and decide, based on this, to institute therapy or make a change in the therapeutic regimen. If the case were somewhat unusual, the physician may further order additional tests (e.g., Adiponectin, C-peptide, hsCRP, etc.). Thus, in the most extended cases, the physician may then have four or five pieces of information, often taken at different time points. (e.g., five test results). While in some situations, the physician will eventually order one or more other tests, the drawback is that the physician does not order these tests all at once and the test results are not integrated into any sort of overall view of the patient condition that can then be related to a drug treatment plan. Thus, one drawback with conventional treatment of the diabetic condition in subjects is the acquisition of the relevant information regarding the condition of the subject in a piecemeal, ad hoc, basis that does not lend itself to determining the overall picture of the subject's condition. Another drawback with conventional treatment of the diabetic condition is the limited database/knowledge on drug classes, limited availability of experts and limited capability to quickly handle the complex nature of anti-diabetic drug data. In multi-drug therapy, the number of choices for a clinician to handle at the drug class level is over 200 alternate regimens, and most classes have multiple suppliers, with some differences between the suppliers.

Furthermore, conventional treatment of the diabetic condition is limited to improving a handful of particular patient conditions, such as improving a precise A1C level (e.g., 6.8% improved to 5.4%). These particular patient conditions are one dimensional, in that each condition describes an exact condition of the patient. If more than one patient condition is to be improved, determining how to treat these conditions individually and in combination becomes rapidly more complex. Accordingly, there exists a need to tailor treatment guidance plans for one or more multi-dimensional conditions, such as general insulin resistance, general beta-cell stress, general cardiovascular risk, etc., in order to determine a general trend of each multi-dimensional condition instead of a specific trend for multiple individual conditions.

Given the above background, what is needed in the art are systems and methods for assessing the condition of a diabetic subject and based on this assessment, offering a suitable personalized treatment plan for the subject.

SUMMARY

The present disclosure addresses the need in the art for systems and methods for assessing the condition of a diabetic subject and offering a suitable treatment plan for the subject based on this assessment. To accomplish this, some embodiments of the present disclosure make an informed selection (e.g., from among over 23,000 different classification patterns). Each classification pattern represents a different permutation of the possible results of the classification variables that are considered by the systems and methods of the present disclosure. A database of these permutations lists the permutations individually, and each such respective permutation is associated with a unique report specific to the respective permutation.

In accordance with the present disclosure, a report is generated for a health professional when a data set is loaded by a partner laboratory into the web portal for the report database. The data is analyzed to create a patient profile, which consists of the pattern of the results. Each pattern has multiple dimensions (e.g., insulin resistance, cardiovascular inflammation, renal condition, etc.) and multiple classifications of such dimensions (e.g., severe, moderately impaired, etc.). The profile, through physician judgement derived decision rules, is linked to a database of information relevant to clinical practice on the major anti-diabetic drug classes. The linkage results in specific content assigned to the report, including an ordering of preferred drug classes, drawn from a content database. This content is divided into many different content blocks, which are used to populate the content of a complete report using complex decision trees, maps, and subsets of the content database. Some of these content blocks map from some set of results to content, or from a set of results to a classification of condition, which is then mapped to content. For example, some of the variables are used to create insulin resistance categories (severe, significant, etc.), which in turn are used to construct a pattern of other factors, encompassing the major aspects of patient condition, which is mapped to specific choices both of drug class order in the drug recommendations sections, and the physician course of action section. Thus there are four steps in this case from a test result of an analyte to specific content in the report (test result to aspect of patient condition to overall patient clinical status to suggested drug order). Other content blocks are static, or drawn from a much more limited set of possibilities. Some map from a result or group of results to content, while others, such as references, are tied to specific wording.

All of these steps and routes to populate content are programmed in accordance with the disclosed systems and methods. In this way all of the content blocks of the report are populated with specific content as soon as a set of results is received. The disclosed systems and methods then generate a report (e.g. in PDF format) that is, in some embodiments, sent electronically to the requesting laboratory. In some embodiments, the database is completely tracked for all changes, and editable by the administrators so that it can be kept up to date.

In the systems and methods in accordance with one aspect of the present disclosure, a patient profile is obtained for a subject in need of treatment or treatment modification. In some embodiments, the patient profile comprises a panel of seven tests that are run from a single blood drawn from the patient. In some embodiments, the resulting biochemistry profile is supplemented by two demographic variables (i) gender and (ii) stage of disease or drug therapy. In some embodiments, partial profiles are not permitted, the data set must be submitted complete (including the seven tests and the two demographic variables), or it is rejected. In some embodiments, each algorithm used in the systems and methods of the present disclosure is adjusted for the individual laboratory cut-offs (binning criteria) that are derived from the assay methods and population adjustments particular to each laboratory's service population. In some embodiments, the seven tests that are run from a single blood draw are high-sensitivity c-reactive protein, adiponectin, intact proinsulin, insulin, C-peptide, HbA1c, and the eGFR. In some embodiments, the tests include one or more additional analytes that define a metabolic condition of a patient, such as a brain analyte, a gut analyte, a beta cell analyte, a liver analyte, a kidney analyte, and/or a cardiovascular analyte.

Another aspect of the present disclosure provides a method for a healthcare profession with a patient treatment plan. The method includes obtaining a biochemical data set, which includes a plurality of test results from a single blood draw of the patient, and a demographic data set for the patient. The plurality of test results of the biochemical data set includes at least three measurements from the group consisting of a high-sensitivity c-reactive protein test, an adiponectin level test, a proinsulin level test, an insulin level test, a C-peptide test, a HbA1c test, and an eGFR level test. The demographic data set includes an indication of a gender of the patient and an enumerated indication of a stage of disease or therapy of the patient. All or a portion of the biochemical data set and the demographic data set are run against a subset of decision rules in a plurality of decision rules. In accordance with a determination that one or more firing conditions of a respective decision rule in the subset of decision rules is fired, a corresponding patient pattern in a plurality of patient patterns is determined as a first patient pattern. A report is prepared based on an identity of the first patient pattern. The report provides a prioritization of intervention class in a priority ordering of intervention classes based on the identity of the first patient pattern.

In some embodiments, the plurality of test results include three, four, five, six, or seven measurements from the group consisting of a high-sensitivity c-reactive protein test, an adiponectin level test, a proinsulin level test, an insulin level test, a C-peptide test, an HbA1c test, and an eGFR test.

In some embodiments, the plurality of test results consists of measurements from a high-sensitivity c-reactive protein test, an adiponectin level test, a proinsulin level test, an insulin level test, a C-peptide test, an HbA1c test, and an eGFR test.

In some embodiments, the plurality of test results consists of measurements of eight, nine, ten, eleven, twelve, thirteen, fourteen, or fifteen measurements from a high-sensitivity c-reactive protein test, an adiponectin level test, a proinsulin level test, an insulin level test, a C-peptide test, an HbA1c test, an eGFR test, and one or more analytes that define a dimension of a patient metabolic condition including a brain analyte, a gut analyte, a beta cell analyte, a liver analyte, a kidney analyte, and a cardiovascular analyte.

In some embodiments, the enumerated indication of a patient's stage of disease or therapy is one of (i) diagnosed as pre-diabetes, (ii) diagnosed with diabetes but not taking a drug (iii) diagnosed with diabetes and taking a first line diabetes drug (iv) diagnosed with diabetes and prescribed multiple diabetes drugs without insulin and (v) diagnosed with diabetes and prescribed multiple diabetes drugs with insulin.

In some embodiments, the prioritization of intervention class includes a prioritization of one or more drug classes including a metformin class, a sodium-glucose cotransporter-2 inhibitor class, a glucagon-like peptide-1 receptor agonists class, a dipeptidyl peptidase-4 inhibitor class, an insulin class, a thiazolidinedione class, a glinides class, and a sulfonylureas class.

In some embodiments, the prioritization of intervention class includes a prioritization of one or more drugs in a respective drug class.

In some embodiments, one or more decision rules in the plurality of decision rules is determined according to an analysis of the biochemical data set and the demographic data of each patient across a cohort population of patients conducted by a plurality of expert physicians.

In some embodiments, one or more decision rules in the plurality of decision rules is determined according to an analysis of at least a peer reviewed reference pertaining to a drug class for treatment of diabetes.

In some embodiments, the prioritization of intervention class includes a prioritization of one or more drug classes, exercise, and diet.

In some embodiments, the report provides a magnitude of anticipated efficacy of the first patient pattern with respect to one or more patient metabolic conditions identified by the biochemical data set.

In some embodiments, the report comprises a plurality of sections. Each section in the plurality of sections is classified as a static section that includes predetermined information, a dynamic section that includes predetermined information as determined by one or more decision rules in the plurality of decision rules, or a reference section that includes information provided from one or more databases that is accessible to the computer.

In some embodiments, each firing condition in the one or more firing conditions of a respective decision rule in the plurality of decision rules includes one or more conditions selected from the group consisting of a diabetes stage of the patient, a number of medications currently being taken by the patient, a dosage of a medication currently being taken by the patient a type of medications currently being taken by the patient, a type of medications previously taken by the patient, and a patient metabolic condition.

In some embodiments, the patient metabolic condition is classified on a non-dimensional scale.

Yet another aspect of the present disclosure provides a method for providing a healthcare professional with a metabolic assessment of a patient. In some embodiments the patient has not been diagnosed with diabetes. In this aspect of the present disclosure, at a computer comprising one or more processors and a memory, a biochemical data set is obtained. The biochemical data set comprises a plurality of test results from a single blood draw of the patient. The plurality of test results comprises at least three measurements from the group consisting of a high-sensitivity c-reactive protein test, an adiponectin level test, a proinsulin level test, an insulin level test, a C-peptide test, a HbA1c test, and an eGFR level test. A demographic data set for the patient is obtained. The demographic data set comprises an indication of a gender of the patient. The biochemical data set and demographic data set is used to map the patient onto a first patient pattern in a plurality of patient patterns. A report is then prepared based on an identity of the first patient pattern. The report provides a metabolic status of the patient.

BRIEF DESCRIPTION OF THE DRAWINGS

FIGS. 5B, 5C, and 5D illustrate a biochemical test result, in accordance with an embodiment of the present disclosure.

FIG. 8 illustrate examples of decision rules that map patient patterns of insulin resistance, β-cell stress level, and cardiovascular inflammation to proposed drug class orders (M=metformin, S=SGLT-2 inhibitors, G=GLP-1 receptor agonists, D=DPP-4 inhibitors, I=insulin, T=thiazolidinediones, and F=Sulfonylureas, and the position of this latter class also is used for Glinides) in which profile combinations of dimensions that define types of profiles map to the proposed drug class orders of drug classes associated with each profile, in accordance with an example embodiment of the present disclosure.

FIG. 9 illustrates a reports database that provides template reports as a collective function of (i) therapy/disease state, (ii) gender, (iii) hs-CRP levels, (iv) adiponectin levels, (v) insulin levels, (vi) C-peptide levels, (vii) HbA1c levels, and (viii) eGFR levels in accordance with an embodiment of the present disclosure.

FIGS. 10A, 10B, 10C, 10D, 10E, 10F, 10G, 10H, 10I, and 10J collectively illustrate an example report that provides diabetes patient treatment guidance for a male patient that has diabetes and that is presently taking multiple drugs with insulin, in accordance with an embodiment of the present disclosure.

FIGS. 10K, and 10L collectively illustrate an example report that provides diabetes patient treatment guidance for a female patient, in accordance with an embodiment of the present disclosure.

Like reference numerals refer to corresponding parts throughout the several views of the drawings.

DETAILED DESCRIPTION

Figure 1:
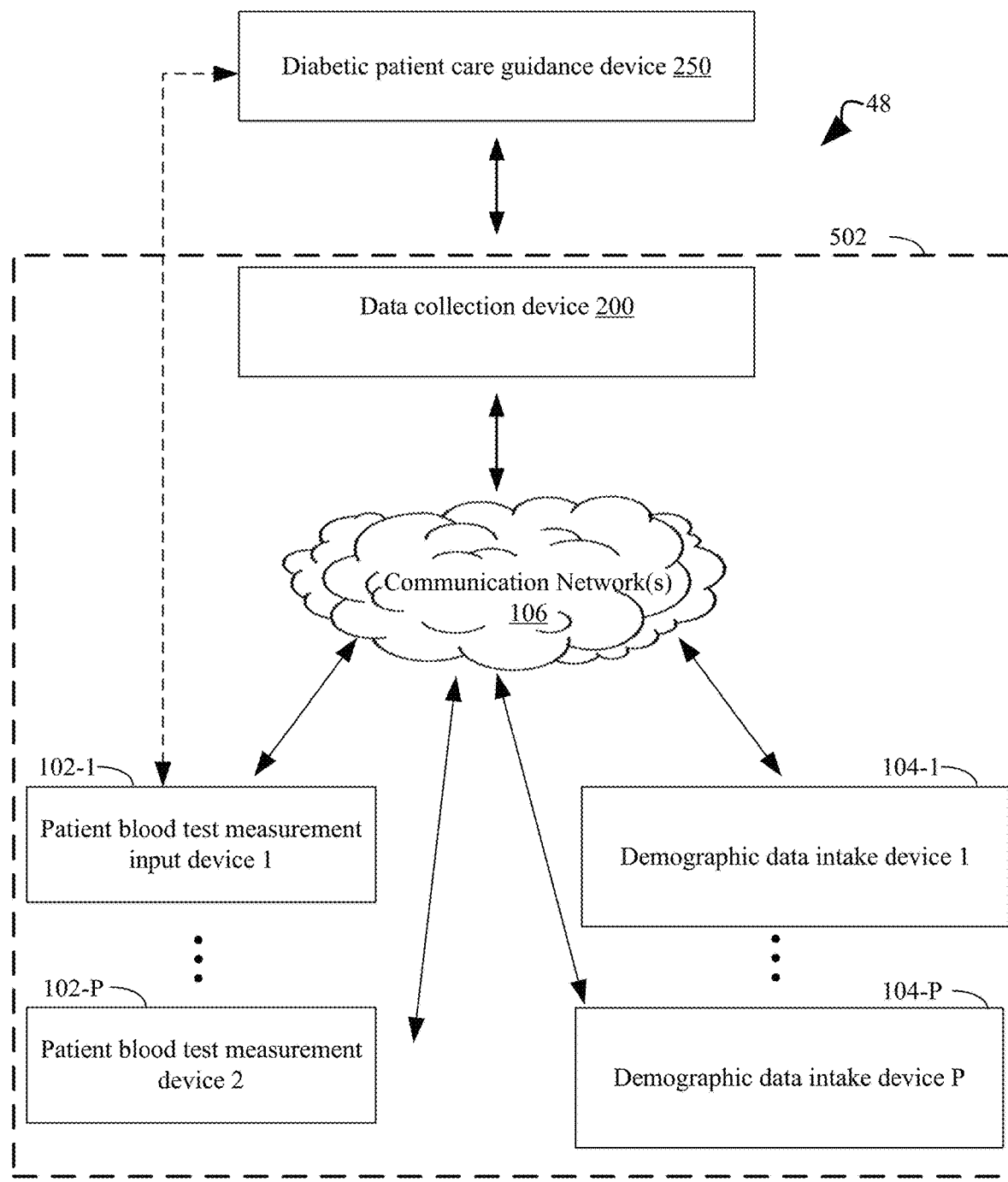
FIG. 1 illustrates an exemplary system topology for providing diabetes patient treatment guidance that includes a diabetes patient care guidance device 250 for providing the treatment guidance, a data collection apparatus 200 for collecting patient biochemical data and demographic data, one or more sensors 102 for measuring the patient biochemical data, and one or more apparatus 104 for obtaining the demographic data, where the above-identified components are interconnected, optionally through a communications network, in accordance with an embodiment of the present disclosure.
Figure 5A:
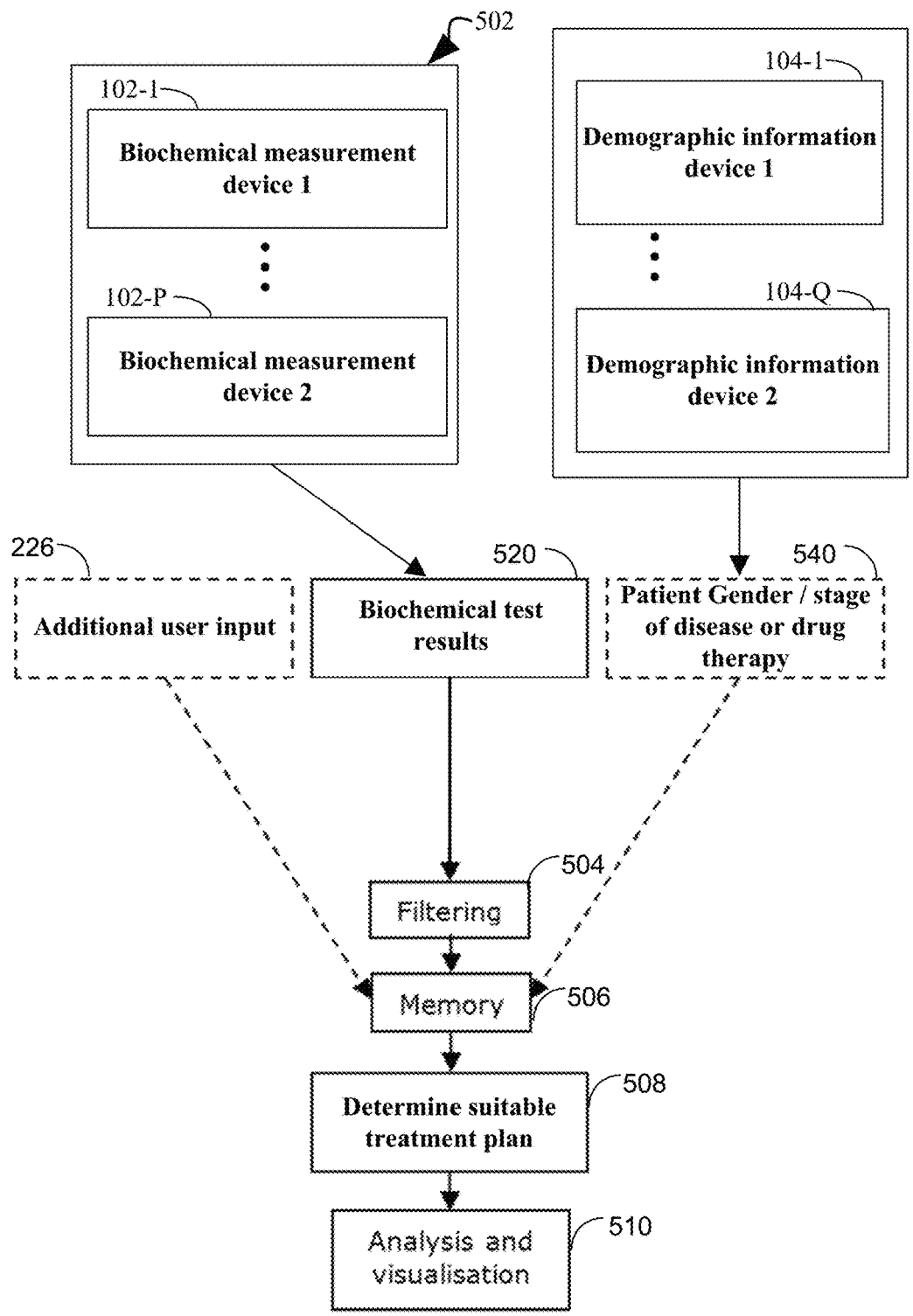
FIG. 5A illustrates an example integrated system of connected measurement devices, demographic information intake devices, memory and a processor for providing diabetes patient treatment guidance for a patient, in accordance with an embodiment of the present disclosure.
Figure 5D:
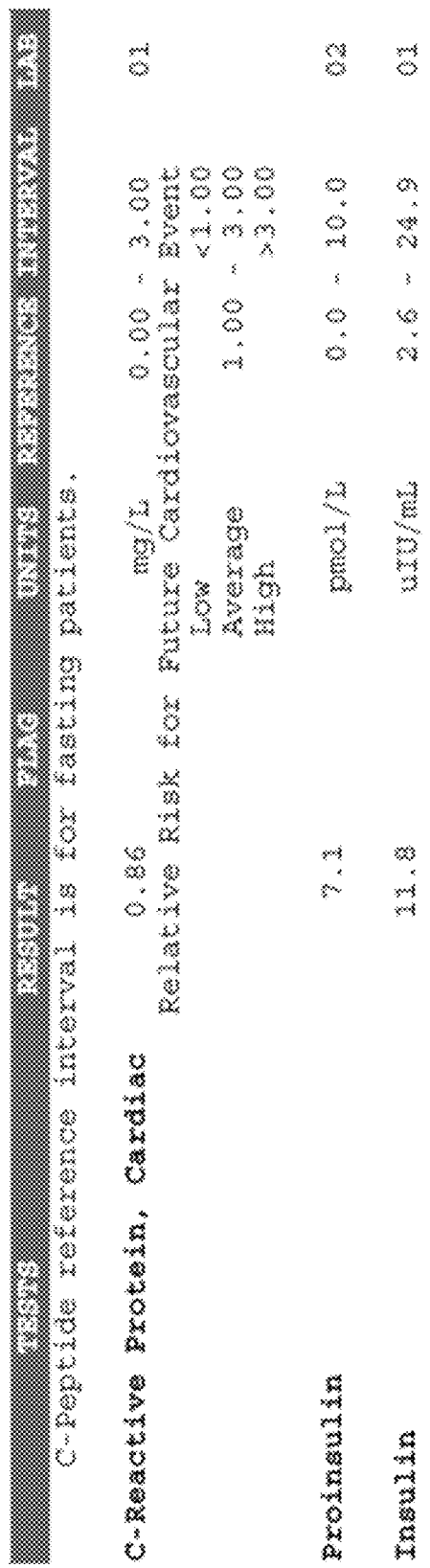

The present disclosure provides systems and methods for providing diabetes patient treatment guidance for a healthcare provider which may be supplemented with appropriate educational materials for the patient. FIG. 1 illustrates an example of an integrated system 502 for providing diabetes patient treatment guidance, and FIG. 5 provides more details of such a system 502. The integrated system 502 includes one or more connected blood test measurement devices 102, one or more demographic data intake devices 104, memory 506, and a processor (not shown) for providing diabetes patient treatment guidance.

With the integrated system, diabetes patient treatment guidance is provided for a patient. For instance, a biochemical data set is obtained from a single blood sample using one or more blood test measurement input devices 102. The biochemical data set comprises test results from at least a single blood draw of the patient including at least three measurements, at least four measurements, at least five measurements, at least six measurements, or seven measurements selected from the set: a high-sensitivity c-reactive protein test, an Adiponectin level test, a proinsulin level test, an insulin level test, a C-peptide test, a HbA1c test, and an eGFR level test. For example, where seven measurements are in the dataset, they include high-sensitivity c-reactive protein test results, adiponectin level test results, proinsulin level test results, an insulin level test results, C-peptide test results, HbA1c test results, and eGFR level test results from a single blood draw. Additional details and information related to the biochemical data set and test results will be described in more detail infra, with particular reference to at least FIGS. 5B, 5C, and 5D. A demographic data set for the patient is also obtained using the demographic intake device 104. In embodiments, where the goal is ranked ordered drug classes for diabetic patient treatment, the demographic data comprises the patient's gender and diabetes stage. In embodiments where the goal is to assess the metabolic state of the patient, the demographic data comprises the patient's gender but may not include diabetes stage. The biochemical data set and demographic data set is used to map the patient onto a first patient pattern in a plurality of patient patterns. Then, a report is prepared based on an identity of the first patient pattern. In some embodiments (e.g., where the goal is ranked ordered drug classes for diabetic patient treatment), the report prioritizes intervention classes for the patient based on the identity of the first patient pattern. In some embodiments (e.g., where the goal is to assess the metabolic state of the patient), the report provides a metabolic state of the subject.

An advantage of the present disclosure is that the report is easily translated into different languages.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first patient could be termed a second patient, and, similarly, a second patient could be termed a first patient, without departing from the scope of the present disclosure. The first patient and the second patient are both patients, but they are not the same patient. Furthermore, the terms "subject," "user," and "patient" are used interchangeably herein.

The terms "device" and apparatus are used interchangeably herein.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 2A:
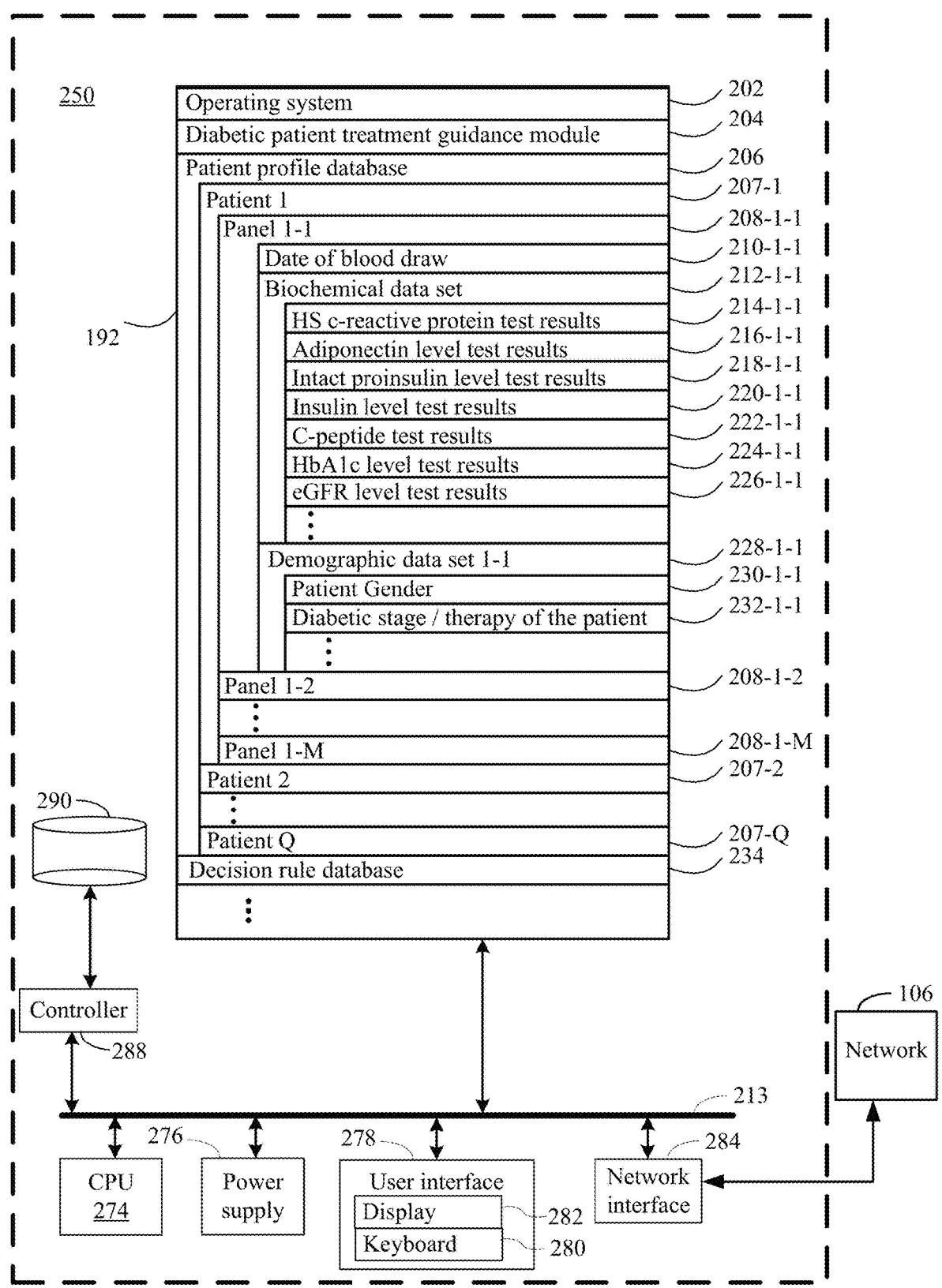
FIG. 2A illustrates an apparatus for providing diabetes patient treatment guidance for a subject in accordance with an embodiment of the present disclosure.
Figure 2B:
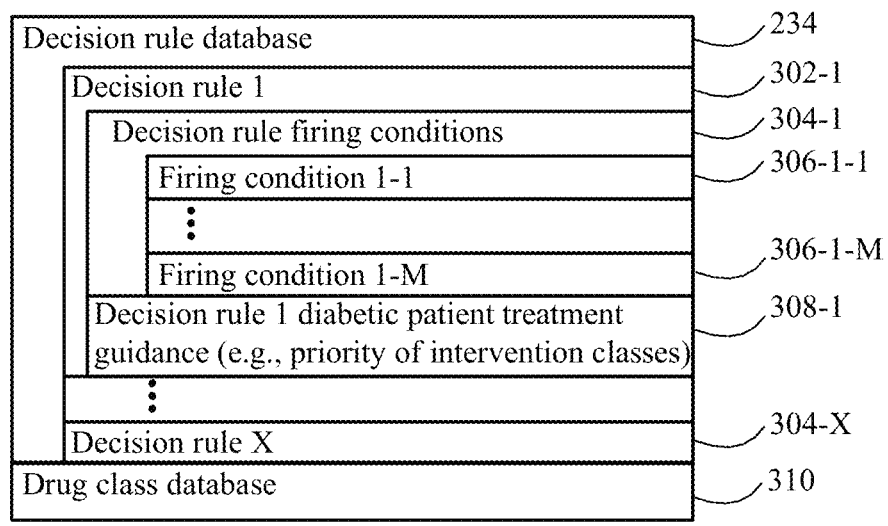
FIG. 2B illustrates a decision rule database for providing diabetes patient treatment guidance for a patient in accordance with another embodiment of the present disclosure.
Figure 3:
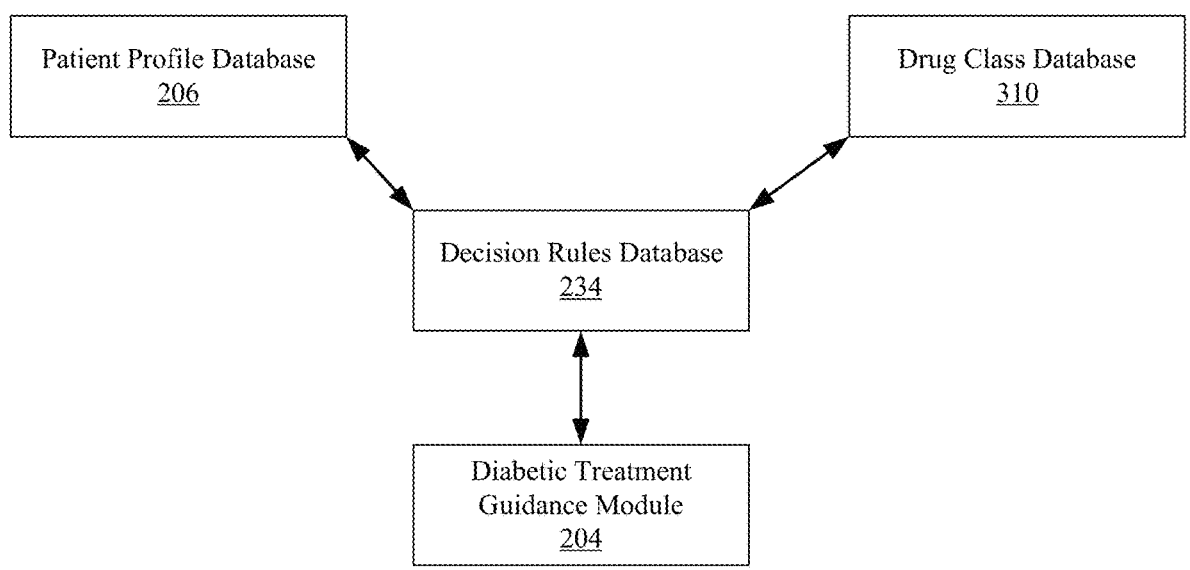
FIG. 3 illustrates a communication scheme between various databases and modules of the diabetes patient care guidance device 250, in accordance with an embodiment of the present disclosure.

A detailed description of a system 48 for providing diabetes patient treatment guidance for a patient in accordance with the present disclosure is described in conjunction with FIGS. 1 through 3. As such, FIGS. 1 through 3 collectively illustrate the topology of the system in accordance with the present disclosure. In the topology, there is a diabetes patient care device 250 for providing diabetes patient treatment guidance for a patient (FIGS. 1, 2, and 3), a device for data collection ("data collection device 200"), one or more blood test measurement devices 102 for obtaining a biochemical data set (FIGS. 1 and 5), and one or more demographic data intake devices for obtaining demographic data. Throughout the present disclosure, the data collection device 200 and the diabetes patient care guidance device 250 will be referenced as separate devices solely for purposes of clarity. That is, the disclosed functionality of the data collection device 200 and the disclosed functionality of the diabetes patient care guidance device 250 are contained in separate devices as illustrated in FIG. 1. However, it will be appreciated that, in fact, in some embodiments, the disclosed functionality of the data collection device 200 and the disclosed functionality of the diabetes patient care guidance device 250 are contained in a single device.

Referring to FIG. 1, the diabetes patient care guidance device 250 provides diabetes patient treatment guidance for a patient. To do this, the data collection device 200, which is in electronic communication with patient care guidance device 250, receives blood test measurements originating from one or more measurement input devices 102. In some embodiments, the blood test measurements are taken from a single blood draw. For instance, in alternative embodiments, the data collection device 200 receives blood test measurements originating from one or more measurement input devices 102, where the blood test measurements are from a plurality of blood draws taken at the same time. Further, the data collection device receives a demographic data set for the patient from one or more demographic data intake devices 104. The demographic data set includes (i) an indication of a gender of the patient and/or (ii) an indication of a diabetes stage of the patient. For instance, in some embodiments the demographic data set includes only an indication of a gender of the patient (e.g., for determining a metabolic status of the patient). In some embodiments, the data collection device 200 receives the biochemical data and demographic data directly from the blood test measurement devices 102 and demographic data intake devices 104. For instance, in some embodiments the data collection device 200 receives this data wirelessly through radio-frequency signals. In some embodiments such signals are in accordance with an 802.11 (WiFi), Bluetooth, or ZigBee standard. In some embodiments, the data collection device 200 receives such data directly, analyzes the data, and passes the analyzed data to the diabetes patient care guidance device 250.

In some embodiments, the data collection device 200 and/or the diabetes patient care guidance device 250 is not proximate to the patient and/or does not have wireless capabilities or such wireless capabilities are not used for the purpose of acquiring the biochemical data or the demographic data. In such embodiments, a communication network 106 may be used to communicate the biochemical data from the one or more blood test measurement input devices 102 to the data collection device 200 and/or the diabetes patient care device 250 and demographic data from the one or more data intake devices to the data collection device 200 and/or the diabetes patient care guidance device 250.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. In some embodiments network 106 is a body area network (BAN) or a personal area network (PAN). The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSDPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

In some embodiments, the blood test measurement device is attached to the patient and the data collection device 200 and/or the diabetes patient care guidance device 250 is part of the measurement device. That is, in some embodiments, the data collection device 200 and/or the diabetes patient care guidance device 250 and the blood test measurement device 102 are a single device. In some embodiments, the data collection device 200 and/or the diabetes patient care guidance device 250 is part of an insulin pen or other form of intervention delivery device. More typically, blood test measurement devices and demographic data intake devices 104 as well as data collection device 200 are part of a single laboratory and/or a single laboratory company, and the diabetes patient care guidance device 250 is part of a consulting service that is remotely located and independent of the laboratory.

Of course, other topologies of the system 48 are possible. For instance, rather than relying on a communications network 106, the one or more blood test measurement devices 102 and the data intake devices 104 may wirelessly transmit information directly to the data collection device 200 and/or the diabetes patient care guidance device 250. Further, the data collection device 200 and/or the diabetes patient care device 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the diabetes patient care guidance device 250 comprises one or more computers. For purposes of illustration in FIG. 2, the diabetes patient care guidance device 250 is represented as a single computer that includes all of the functionality for providing diabetes patient treatment guidance for a patient. However, the disclosure is not so limited. In some embodiments, the functionality for providing diabetes patient treatment guidance for a patient is spread across any number of networked computers and/or resides on each of several networked computers and/or is hosted on one or more virtual machines at a remote location accessible across the communications network 106 of skill in the art will appreciate that any of a wide array of different computer topologies are used for the application and all such topologies are within the scope of the present disclosure.

Turning to FIG. 2 and FIG. 3 with the foregoing in mind, an exemplary diabetes patient care guidance device 250 for providing diabetes patient treatment guidance for a patient comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the diabetes patient care guidance device 250 but that can be electronically accessed by the diabetes patient care guidance device 250 over an Internet, intranet, or other form of network or electronic cable (illustrated as element 106 in FIG. 2) using network interface 284.

In some embodiments, the memory 192 of the diabetes patient care guidance device 250 for providing diabetes patient treatment guidance for a patient stores:

an operating system 202 that includes procedures for handling various basic system services;

a diabetes patient treatment guidance module 204 that facilitates generating a report for a respective patient, and storing a one or more previously generated reports;

a patient profile database 206 for a plurality of patients, the patient profile database comprising for each patient 207 in the plurality of patients, one or more panel 208, each such panel associated with a date of blood draw 210, a biochemical data set 212 based on this blood draw, and a demographic data set 238, the biochemical data set 212 comprising hs c-reactive protein test results 214, adiponectin level test results 216, proinsulin level test results 218, insulin level test results 220, C-peptide level test results 222, HbA1c level test results 224, and/or eGFR level test results 226, and the demographic data set 228 comprising patient gender 230 and the diabetes stage of the patient and/or stage of drug therapy 232 of the patient;

a decision rule database 234 that comprises a plurality of decision rules 302, each decision rule 302 comprises a plurality of decision rule firing conditions 304 and corresponding patient treatment guidance 308; and a drug class database 310 that comprises a listing of one or more drug classes (e.g., metformin class, DDP-4 class, etc.).

In some embodiments, the diabetes patient treatment guidance module 204 is accessible within any browser (phone, tablet, laptop/desktop). In some embodiments, the diabetes patient treatment guidance module 204 runs on native device frameworks, and is available for download onto a diabetes patient care guidance device 250 running an operating system 202 such as Android or iOS. In some embodiments, the diabetes patient treatment guidance module 204 communicates with the patient profile database 206 and the decision rule database 234 in order to facilitate generating a report for each respective patient. In some embodiments, each generated report is stored in within the diabetic patient treatment guidance module 204 for future use. These future uses include creating a historical record of reports for each respective patient, as well as analyzing past reports and current patient status to determine trends of treatment guidance efficacy.

In some embodiments, the patient profile database 206 comprises a collection of patient profiles. Each patient profile includes a plurality of markers (e.g., analytes), that are determined from a biochemical test (e.g., test results of FIGS. 5B, 5C, and 5D) and/or provided by the respective patient. Each marker describes a condition and/or aspect of the patient, and may include one or more gradations of the respective marker. For instance, in some embodiments more than one set of biochemical data is provided for a patient, and accordingly a gradation is determined from one or more changes in the sets of biochemical data (e.g., a large increase in sodium level yields a large gradation). In some embodiments, each marker includes an associated non-dimensional indicator (e.g., severe, moderately impaired, elevated, depressed, etc.). In some embodiments, each patient pattern reflects a particular mapping of patient conditions, such that each possible permutation of one or more patient conditions is associated with a respective patient pattern (e.g., a low insulin level and high albumin to creatinine ratio is associated with a first patient pattern, a low insulin level and low albumin to creatinine ratio is associated with a second patient pattern, a high insulin level and high albumin to creatinine ratio is associated with a third patient pattern, etc.) In some embodiments, the patient profile database 206 comprises a plurality of patient patterns. In some embodiments, the plurality of patient patterns comprises at least 10,000 patient patterns. In some embodiments, the plurality of patient patterns comprises at least 15,000 patient patterns. In some embodiments, the plurality of patient patterns comprises at least 20,000 patient patterns. In some embodiments, the plurality of patient patterns comprises at least 25,000 patient patterns.

In some embodiments, the decision rule database 234 stores one or more decisions rules 302. Each decision rules comprises one or more decision rule firing conditions 304. In accordance with a determination that a decision rule firing condition 304 is satisfied, the respective decision rule 302 is fired. In some embodiments, firing of a decision rule 302 up-weights an associated treatment guidance plan and/or patient pattern. Moreover, in some embodiments each decision rule is derived from an opinion of an expert physician (e.g., includes physician recommendations). For instance, in some embodiments a plurality of expert physicians determines one or more decision rules 302. In some embodiments, the one or more decision rules are determined on a consensus basis within the plurality of expert physicians. In some embodiments, each decision rule 302 and treatment guidance 308 have a one-to-one relationship. However, the present disclosure is not limited thereto. In some embodiments, each decision rule 302 and treatment guidance 308 have a one-to-many relationship. Furthermore, in some embodiments decision rules 302 and treatment guidance 308 have a many-to-one relationship. Furthermore, in some embodiments the decision rule database 234 is updated on a continual (e.g., recurring basis) in order to provide and incorporate the most up-to-date information.

In some embodiments, the drug class database 310 comprises a listing of one or more drug classes. These drug classes include, but are not limited to, a metformin class, a SGLT-2 inhibitor class, a GLP-1 receptor agonist class, a DPP-4 inhibitor class, an insulin class, a thiazolidinedione class, a Sulfonylureas class, and a Glinides class. In some embodiments, each class listing includes a listing of specific drugs for the respective drug (e.g., a listing of each specific metformin drug available in a market). In some embodiments, the listing of specific drugs includes a dosage of each drug, a manufacturer of each drug, an indication if the drug is covered by one or more insurance providers, a dosage of each drug, a cost of each drug, an availability of each drug, etc. In some embodiments, the drug class database 306 comprises a record of literature related to diabetes drug classes and/or metabolic drug classes. In some embodiments, the record of literature includes some or all published academic papers, publically available patient data, and the like. Furthermore, in some embodiments the drug class database 310 is updated on a continual (e.g., recurring basis) in order to provide and incorporate the most up-to-date information.

Referring to FIG. 3, a communication scheme between various databases and modules of the diabetes patient guidance device 250 will be described in detail, in accordance with an embodiment of the present disclosure. In some embodiments, in accordance with a determination that a type of report is determined (e.g., a diabetes treatment report and/or a metabolic status report), the patient profile database 206 provides information (e.g., patient panel 208) related to desired report to the decision rule database 234. This information provided by the patient profile database 206 is run against the decision rules 302 of the decision rules database 302, with each fired decision rule 302 up-weighting a particular patient pattern. In some embodiments, pertinent information is provided from the drug class database to the decision rule database 234 in order to account for such information in determining a patient pattern. This information includes information that is pertain to the respective patient relating to specific drugs and/or drug classes, such as an availability of a specific drug and/or drug class, or a price of a specific drug. Accordingly, if the respective patient has one or more limitations regarding a particular drug and/or drug class, these limitations are accounted for in determining a patient pattern for the respective patient. In accordance with a determination that a patient pattern is selected for the respective patient (e.g., a first patient pattern; a highest-weighted patient pattern), the patient pattern is provided to the diabetic treatment guidance module 204. The diabetic treatment guidance module 204 selects relevant reporting content to include in the respective patient report, which is compiled into an appropriate format (e.g., the format depicted in FIG. 10).

In some embodiments, one or more of the above identified data elements or modules of the diabetes patient care guidance device 250 for providing diabetes patient treatment guidance for a patient are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. For instance, in some implementations the decision rules database 234 and the drug class database 310 are subsumed as a single database (e.g., information pertaining to drug class and/or specific drug limitations is included in respective decision rules 302). In some implementations, the memory 192 and/or 290 optionally stores a subset of the modules and data structures identified above. Furthermore, in some embodiments, the memory 192 and/or 290 stores additional modules and data structures not described above.

In some embodiments, a diabetes patient care guidance device 250 for providing diabetes patient treatment guidance for a patient is a smart phone (e.g., an iPHONE), laptop, tablet computer, desktop computer, or other form of electronic device (e.g., a gaming console). In some embodiments, the diabetes patient care guidance device 250 is not mobile. In some embodiments, the diabetes patient care guidance device 250 is mobile.

It should be appreciated that the diabetes patient care guidance device 250 illustrated in FIG. 2 is only one example of a multifunction device that may be used for providing diabetes patient treatment guidance for a patient, and that the diabetes patient care guidance device 250 optionally has more or fewer components than shown, optionally combines two or more components, or optionally has a different configuration or arrangement of the components. The various components shown in FIG. 2 are implemented in hardware, software, firmware, or a combination thereof, including one or more signal processing and/or application specific integrated circuits.

While the system 48 disclosed in FIG. 1 can work standalone, in some embodiments it can also be linked with electronic medical records to exchange information in any way.

Figure 4:
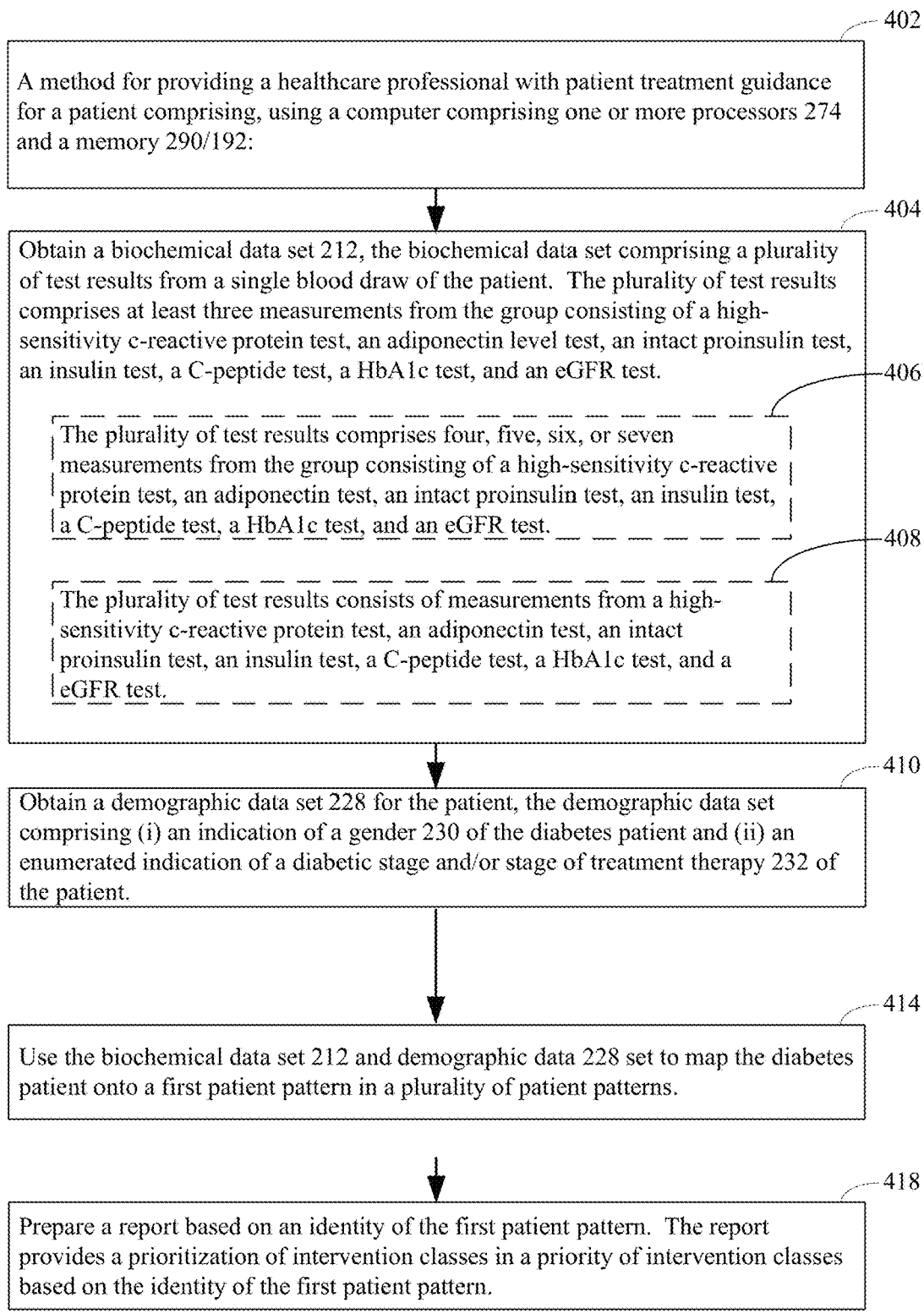
FIG. 4 provides a flow chart of processes and features of an apparatus for providing diabetes patient treatment guidance for a patient, where optional elements of the flow chart are indicated by dashed boxes, in accordance with various embodiments of the present disclosure.

Now that details of a system 48 for providing diabetes patient treatment guidance for a patient have been disclosed, details regarding a flow chart of processes and features of the system, in accordance with an embodiment of the present disclosure, are disclosed with reference to FIG. 4. In some embodiments, such processes and features of the system are carried out by the basal/bolus diabetes patient treatment guidance module 204 illustrated in FIG. 2.

Block 402.

With reference to block 402 of FIG. 4, the goal of diabetes therapy is to match as closely as possible suitable interventions, such as anti-diabetic agents, with the patient's specific diabetes condition. As illustrated in FIG. 2, a diabetes patient care guidance device 250 comprises one or more processors 274 and a memory 192/290. The memory stores instructions that, when executed by the one or more processors, perform a method for providing diabetes patient treatment guidance for a patient.

Blocks 404-408.

In the method, a biochemical data set 212 is obtained. The biochemical data set comprises a plurality of test results from a single blood draw of the patient. In some embodiments, the plurality of test results comprises at least four measurements from the group consisting of high-sensitivity c-reactive protein test results 214, adiponectin level test results 216, proinsulin level test results 218, insulin level test results 220, C-peptide test level results 222, HbA1c test level results 224, and eGFR level test results 226. In some embodiments, the biochemical data set comprises Referring briefly to FIGS. 5B, 5C, and 5D, an exemplary biochemical data set is depicted as one or more test results. In some embodiments, the test results which comprise the biochemical data include a complete blood count (CBC), including a white blood cell count, a red blood cell count, Hemoglobin, Hematocrit, a mean corpuscular volume (MCV), a mean corpuscular hemoglobin (MCH), a mean corpuscular hemoglobin concentration (MCHC), a red blood cell distribution width (RDW) a platelet indicator, as well as an absolute and/or percent based reading for Neutrophils, Lymphocytes, Monocytes, Eosinophils, and Basophils. In some embodiments, the test results which comprise the biochemical data include a complete metabolic panel (e.g., a 14-part metabolic panel). In some embodiments, the test results which comprise the biochemical data include a liquid panel with non-high-density lipoprotein cholesterol (LP+ Non HDL cholesterol) test. In some embodiments, the test results which comprise the biochemical data include a Hemoglobin A1c test. In some embodiments, the test results which comprise the biochemical data include an adiponectin test. In some embodiments, the test results which comprise the biochemical data include a C-peptide serum test. In some embodiments, the test results which comprise the biochemical data include C-reactive protein cardiac test. In some embodiments, the test results which comprise the biochemical data include a proinsulin test. In some embodiments, the test results which comprise the biochemical data include an insulin test. In some embodiments, the test results which comprise the biochemical data include an analyte determined from a venipuncture draw. In some embodiments, the test results include additional quantifiable markers, such as a urinalysis test, a cardiovascular test, a kidney function test, etc.

Referring to block 406 of FIG. 4, in some embodiments, the plurality of test results comprises one, two, three, four, five, six, or seven measurements from the group consisting of high-sensitivity c-reactive protein test results 214, adiponectin level test results 216, proinsulin level test results 218, insulin level test results 220, C-peptide test level results 222, HbA1c test level results 224, and eGFR level test results 226. In some embodiments, the plurality of test results comprises one or more additional metabolic condition analytes of a patient including one or more brain analytes (e.g., ghrelin receptor), one or more adipose tissue analytes (e.g., leptin), one or more gut analytes (e.g., gastric inhibitor polypeptide (GIP)), one or more beta cell or pancreatic analytes (e.g., glucagon, pancreatic beta-cell insulin release), one or more liver function analytes (e.g., aspartate aminotransferase (AST) to alanine aminotransferase (ALT) ratio, gamma-glutamyltransferase, bile acids, etc.), one or more kidney analytes (e.g., cystatin, uric acid production, etc.), and/or one or more cardiovascular analyses (e.g., blood pressure, troponin, NT-BNP, matrix metallopeptidase 9 (MMP-9), etc.). Accordingly, in some embodiments the plurality of test results includes one, two, three, for, five, six, seven, eight, nine, ten, eleven, twelve, thirteen, fourteen, fifteen, or sixteen measures from the above described analytes and test results. In some embodiments, each test result and/or analyte is a multi-dimensional condition, such that the test results describe more than one condition or dimension of a patient. For instance, a cardiovascular analyte of a blood pressure reading is considered multidimensional since blood pressure readings include a systolic blood pressure and a diastolic blood pressure. Accordingly, information can be inferred from the overall blood pressure, the systolic blood pressure, and/or the diastolic blood pressure of the patient. As another non-limiting example, in some embodiments beta-cell secretion is a multi-dimensional condition as the condition includes insulin secretion and C-peptide secretion. As the medical industry continues to evolve and progress, additional anatyes may be determined to be particularly useful in diabetes treatment, and thus included in the present disclosure. Thus, recording these analytes may be of use for implementations in future patient patterns and reports. Furthermore, in some implementations a physician requests a particular analyte to be determined or test to be conducted, which is included within the biochemical data set of the respective patient.

Referring to block 408 of FIG. 4, in some embodiments the plurality of test results consists of high-sensitivity c-reactive protein test results 214, adiponectin level test results 216, proinsulin level test results 218, insulin level test results 220, C-peptide test level results 222, HbA1c test level results 224, and eGFR level test results 226.

By way of non-limiting example, a C-peptide test measures the level of C-peptide test in the blood. It is generally found in amounts proportional to insulin because insulin and C-peptide are linked when first made by the pancreas. A C-peptide test can be done when diabetes has just been found and it is not clear whether type 1 diabetes or type 2 diabetes is present. A person whose pancreas does not make any insulin (type 1 diabetes) has a low level of insulin and C-peptide. A person with type 2 diabetes can have a normal or high level of C-peptide. A C-peptide test can also help find the cause of low blood sugar (hypoglycemia), such as excessive use of medicine to treat diabetes or a noncancerous growth (tumor) in the pancreas (insulinoma). Because man-made (synthetic) insulin does not have C-peptide, a person with a low blood sugar level from taking too much insulin will have a low C-peptide level but a high level of insulin. An insulinoma causes the pancreas to release too much insulin, which causes blood sugar levels to drop (hypoglycemia). A person with an insulinoma will have a high level of C-peptide in the blood when they have a high level of insulin.

By way of another non-limiting example, the high-sensitivity CRP (hs-CRP) test is used to check for cardiovascular disease. In some instances, hs-CRP level of lower than 1.0 mg/L indicated low risk of CVD (heart disease), hs-CRP level of 1.0 mg/L and 3.0 mg/L means a moderate risk of CVD, and hs-CRP level of more than 3.0 mg/L indicates a high risk of CVD.

Blocks 410-412.

Referring to blocks 410 and 412 of FIG. 4, the method further includes obtaining a demographic data set 228 for the patient, the demographic data set comprising (i) an indication of a gender 230 of the patient (e.g., patient) 207 and/or (ii) an enumerated indication of a diabetes stage and/or stage of treatment therapy 232 of the patient 207. In some embodiments, the enumerated indication of a diabetes stage of the patient is one of (i) diagnosed as pre-diabetes, (ii) diagnosed with diabetes but not taking a drug (iii) diagnosed with diabetes and taking a first line diabetes drug (iv) diagnosed with diabetes and prescribed multiple diabetes drugs without insulin and (v) diagnosed with diabetes and prescribed multiple diabetes drugs with insulin. In some embodiments, the enumerated indication of a diabetes stage of the patient includes one or more subdivisions of the above described stages (e.g., a subdivision of a diabetic stage and/or a subdivision of a treatment therapy), such as a subdivision that includes patients diagnosed with diabetes and only taking metformin. In some embodiments, the demographic data set includes biometric information of the respective patient including a height of the patient, a weight of the patient, an age of the patient, etc.

Block 414.

Referring to block 414 of FIG. 4, the method further includes using the biochemical data set 212 and demographic data 228 set to map the patient onto a first patient pattern in a plurality of patient patterns. In some embodiments, this comprises running the biochemical data set 212 and demographic data 228 against a series of decision rules 302 in order to identify a drug class order. In some embodiments, the series of decisions rules 302 include each decision rule stored in the decision rule database 234. In some embodiments, the series of decision rules 302 include a subset selected from all of the decision rules stored in the decision rule database 234. For instance, in some embodiments depending on information provided by the biochemical data set 212 and the demographic data 228, one or more decision rules 302 is not application (e.g., a decision rule dedicated to a metabolic status of a patient is not utilized in generating a diabetes treatment guidance report). As illustrated in FIG. 2B, a decision rule 302 includes a number of firing conditions 306 and one or more associated treatment guidance 308 that is provided if this decision rule is fired. In some embodiments, firing of a respective decision rule up-weights a respective treatment guidance 308 and/or patient pattern. Accordingly, in some embodiments if more than one decision rule is fired, the respective treatment guidance 308 and/or patient pattern that is up-weighted the most is determined to be the most relevant guidance and/or pattern (e.g., a first patient pattern). However, the present disclosure is not limited thereto. For instance, in some embodiments only one decision rule 302 is fired as each decision rule encompasses a unique set of firing conditions that differentiate a first decision rule from a second decision rule. FIG. 8 provides a partial example of such decision rules 302. For example, drawing upon biochemical data set 212 and demographic data 228 set, the firing conditions 306 of decision rule 302-1 specify that insulin resistance is severe (condition 306-1), β-cell stress is significant (condition 306-2), and cardiovascular risk is high (306-3). If these firing conditions are satisfied, associated treatment guidance 308 in the form of a drug class order proposal is provided. In typical embodiments only a single drug class order is provided. However, the present disclosure is not limited thereto. For instance, in some embodiments, two drug class orders are provided, three drug class orders are provided, four drug class orders are provided, five drug class orders are provided, six, drug class orders are provided, seven drug class orders are provided, eight drug class orders are provided, nine drug class orders are provided, ten drug class orders are provided, eleven drug class orders are provided, or twelve drug class orders are provided. In some embodiments, the number of drug class orders that are provided is not limited to a particular number, such that each suitable (e.g., relevant) drug class order is provided for a physician to consider. In FIG. 8, and throughout the present disclosure, M=metformin, S=SGLT-2 inhibitors, G=GLP-1 receptor agonists, D=DPP-4 inhibitors, I=insulin, T=thiazolidinediones, and F=Sulfonylureas, and the position of this latter class also is used for Glinides.

Figure 6:
FIG. 6 illustrates the effect that different forms of antidiabetic agent interventions respectively have on (i) fasting glucose levels, (ii) oral glucose tolerance test results, and (iii) HbA1c test results from a pre-administration baseline, in which, in conjunction with FIG. 7, size of arrow shows magnitude of effect: large, intermediate, or small, and shading of arrow or circle shows the type of effect: solid fill being beneficial, no fill being adverse, and hashed being neutral, in accordance with an embodiment of the present disclosure.
Figure 7:
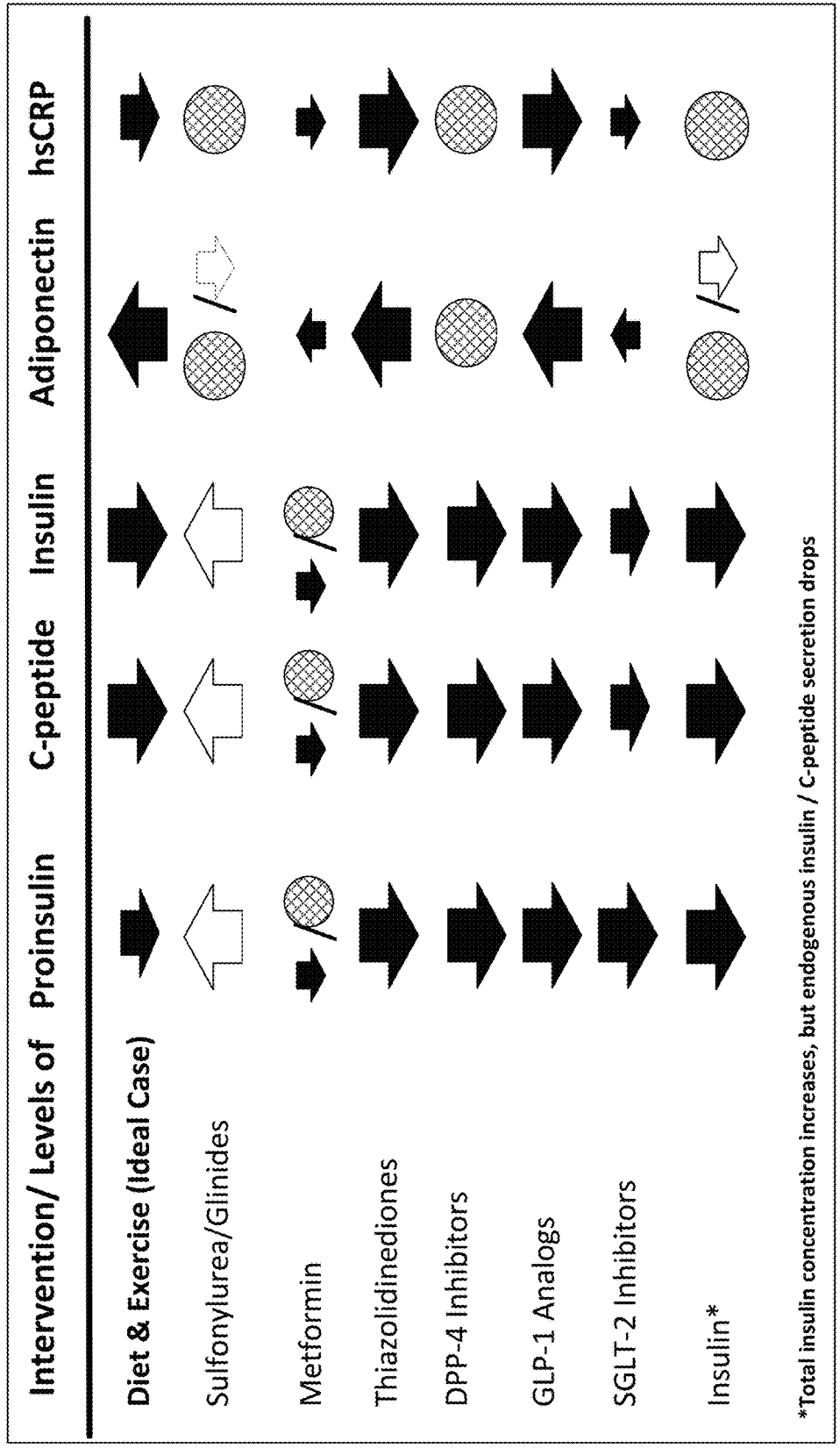
FIG. 7 illustrates the affect that different forms of antidiabetic agent interventions respectively have on (i) proinsulin levels, (ii) C-peptide levels, (iii) insulin levels, (iv) adiponectin levels, and high-sensitivity CRP levels, in which size of arrow shows magnitude of effect: large, intermediate, or small, and shading of arrow or circle shows the type of effect: solid fill being beneficial, no fill being adverse, and hashed being neutral, in accordance with an embodiment of the present disclosure.

Several steps are involved in training the firing conditions 306 and associated treatment guidance 308 for each decision rule 302. First, suitable firing conditions 306 need to be identified. This involves elucidating the physiological pathway underlying patient patterns. This work includes taking biochemical data sets 212 from a number of patients, decomposing the data, sometimes down to one element of the data (e.g. HbA1c levels), sometimes down to three or four interrelated elements of the data, and combining such data, for example, to form and scale suitable patient classifications (e.g., that this aspect of a patient is mild and that one is severe and the next moderate, etc.). FIGS. 6 and 7 illustrate. As illustrated in FIG. 6, diet and exercise lowers patient fasting glucose, improves patient oral glucose tolerance test results, lowers HbA1C levels, lowers proinsulin levels, lowers C-peptide levels, lowers insulin levels, raises adiponectin levels, and lowers high sensitivity CRP levels. On the other hand, drugs in the sulfonylurea/glinide classes lower patient fasting glucose, improve patient oral glucose tolerance test results, lower HbA1C levels, but raise proinsulin levels, raise C-peptide levels, raise insulin levels, and have a marginal effect on adiponectin levels and high sensitivity CRP levels. As such, this informs the basis for making decisions rules that includes in the patient's treatment guidance 308 advice regarding order of precedence of sulfonylurea/glinide classes of drugs. As such, once suitable patient classifications that track observed physiological pathway and underlying patient patterns have been identified and scaled, the linkage step of forming decision rules 302 for the doctors that link firing conditions (e.g., classifications in the form of scaled ranges of particular patient data) 306 to diabetes patient treatment guidance 308 (e.g., recommended drug profiles that specify an order of precedence of drug classes or other forms of intervention, including, in some instances, recommendations on disfavoring certain drug classes for a particular set of firing conditions). As such, the diabetes patient treatment guidance 308 associated with a given decision rule 302, in the form of a drug profile (order of precedence of drug therapies), is a combination of the arrow chart data provided in FIGS. 6 and 7. For instance, the arrow chart data provided in FIGS. 6 and 7 allows for one to predict patient outcomes under several different "what-if" scenarios in which a patient with, for example, no drug on board, given their panel 208 comprising a biochemical data set 212 and demographic data set 228, and then add the drug classes. For instance, how much some hypothetical therapy combination would affect levels of markers measured in the biochemical data set 212. Moreover, FIGS. 6 and 7 illustrate not only whether a given drug class affects a marker present in the biochemical data set 212, it also provides, based on size of the arrow a magnitude of the effect. In some embodiments, the magnitude of the effect is depicted as a color gradation (e.g., red has a severe effect, yellow has a mild effect, green has a no effect). In this way, FIGS. 6 and 7 look, from a drug naïve state for each particular drug class, at what changes to the relevant markers 214 through 226 in the biochemical data set 212 are achieved. This information in FIGS. 6 and 7 provides general guidance about how certain drug classes affect key markers 214 through 226 in the biochemical data set 212 but not quite at the same detailed level of being able to exactly predict what can be expect from the impact on a particular pattern, because the data in FIGS. 6 and 7 represent the marker delta of going from no drug to having drug on board. As such, it is the linkage between each drug and its effect on the markers that calls for physician judgment between the profile of a patient given the marker values 214 through 226 of a given biochemical data set and markers 230 and 232 of a demographic data set from a panel 208 of a patient 207 and the characteristics of each drug class used to treat diabetes patients. Importantly, the clinical judgment from advisory physicians serves an important role because the multi-factorial nature of the decision on ordering drug classes varies widely over the range of possible patient profiles, and is further frequently changing, so the ordering decision is extraordinarily difficult to mathematically model in a way that would be generally accepted, and applicable to all plausible patient biochemical data and/or demographic data profiles, particularly over time. Advantageously, the disclosed systems and methods of the present disclosure are set up to accommodate this dynamic. Further, the disclosed systems and methods make use of numerous reference articles and a panel of advisory physicians that have assessed such data, and other data, in order to develop decision rules for specific sets of trigger conditions, where each such decision rule 302 provides a drug class order, among other forms of diabetes patient treatment guidance, for a given set of marker values in the biochemical data set 212 and demographic data set 228.

Referring to FIG. 8, in some embodiments, the diabetes patient treatment guidance 308 includes a drug class order. Each drug class order provides interpretation to preferably use one drug class before another because it would have more impact given the profile of the marker values of the patient (e.g., elements 214 through 226) in the biochemical data set 212 and marker values (e.g. elements 230 and 232) in the demographic data set 228 for a given patient. Thus, if the diabetes patient treatment guidance 308 specifies the drug class order (M, S, G), then metformins (M) are deemed to have more beneficial impact then SGLT-2 inhibitors (S) which in turned are deemed to have more beneficial impact than GLP-1 receptor agonists (G). In other words, if the diabetes patient treatment guidance 308 of a given decision rule 302 has placed treatment Class A ahead of treatment Class B, then, in accordance with the systems and methods of the present disclosure, based on the medical judgment of experts consulted in developing the disclosed invention, drug Class A is deemed to have a better overall impact on patient condition given the marker values in a panel 208 comprising the biochemical data set 212 and demographic data set 228 of that patient. As such, decision rules 302 provide information on how a given drug class effects a given patient condition by uniquely linking marker values in the biochemical data set 212 and demographic data set to patient outcome upon treatment with the given drug class. As such the disclosed decision rules 302 provide information on both ends of the linkage (marker to patient guidance) based upon expert consensus regarding which drug class is better for a given set of patient marker values (e.g., elements 214 through 226 and elements 230 and 232 of FIG. 2). In so doing the expert consensus makes informed judgments about what is important in the profile (e.g., values for elements 214 through 226 as well as elements 230 and 232 of FIG. 2) as those elements relate to the likelihood of efficacy and optimization of drug therapy.

In the literature, as new drugs and drug classes to treat diabetes are introduced, they are backed by a substantial amount of published comparative information that compares these new newer drugs and drug classes to very old ones. As such, the published literature rarely compares a new drug entrant against another new one. Moreover, rather than establish that the new drug is more efficacious than existing drugs, the trend for introducing a new drug to market has been, and is, to simply establish that the new drug is not inferior to existing drugs. That is, the new drug is as good as the comparator drug that is already been approved by a regulatory agency such as the United States Food and Drug Administration. As such, published studies for new drugs that are sponsored by their manufactures are geared to establish non-inferiority in order to support drug approval, as opposed to tackling the more complex task of establishing which drug is best to improve a diabetic condition. While such information is helpful to the drug company seeking drug approval, such studies are inadequate for assisting a clinician (e.g., physician, nurse practitioner, or similar health professional) in trying to decide which drug or drug class is best for a given diabetes patient's condition. This is particularly the case in many instances where such new drug studies are deliberately designed to generate data that will show that they have the same efficacy as another existing, approved drug. As such, publications concerning the efficacy of new drugs are based on an overall objective (not inferior to, just as efficacious as) that is the exact opposite of generating information that would help a physician to make a difficult decision on which drugs or drug classes to select from for a given patient.

One approach to forming the decision rules 302 is to evaluate each literature and/or non-published information for each respective drug class. Evaluating literature as it is produced allows for the most recent quantification of how the respective drug class will change the values of markers in the biochemical dataset 212. In some embodiments, such evaluation needs to also consider how the values of markers, or combination of markers, in the biochemical dataset 212 will change given the values of the markers in the demographic dataset 223. In some embodiments, the evaluation is conducted by a plurality of expert physicians. Accordingly, in some embodiments each piece of literature is evaluated by a subset of the expert physicians. In so doing, decision rules 302 are formulated and the assay results from the patient, in the form of the biochemical data set 212 and the demographic data set 228 from the patient are then used to find the decision rule that best matches the patient condition and thus has a maximal beneficial impact on the patient.

As such, a central tenet of some embodiments of the systems and methods of the present disclosure is that the physician submitting the biochemical data set 212 and demographic data set in block 410 for analysis by the diabetes patient treatment guidance module 204 in accordance with block 414 indicate the stage of disease or therapy 232 of the patient. One reason for this is that diabetes has discrete stages, and different drugs, or drug combinations, work better at different stages of the disease. For example, the early stages, when a patient is prediabetes, or they are newly diagnosed, and they still have not taken a drug for diabetes, defines an essential stage of disease. Stages beyond this initial stage, once the patient is already being treated, are difficult to ascertain because in a sense, it is not readily possible to distinguish from the marker values 214 through 226 of the biochemical data set the stage the disease is in because they are under treatment. In such instances the drugs the patient is taking have various effects on the values of these markers. As a consequence, as soon as you put the drug in the mix of factors to consider when developing diabetes patient treatment guidance, it obscures what is the underlying condition versus what is the impact of the drug.

To address such situations, the systems and methods of the present disclosure rely upon multiple firing conditions 302 for each decision rule 308. For example, consider the case where patient 1 is simply taking their very first drug, and they are on a pill, which is typical, usually that is a first line of treatment. And such first line drugs tend to have fairly narrow action, primarily controlling sugar, not really addressing much of anything on the underlying level regarding the diabetic condition. That patient is in a completely different situation with respect to what treatment options might make sense next, versus a second patient who is already on two drugs where one is insulin and one is a multi-action pill, and there is already a substantial amount of different effects from the two drugs that are on board. Determining the diabetes patient treatment guidance for the second patient requires taking into account that context (e.g., using firing conditions 306) that they are already taking two drugs that do a lot to change marker values in the biochemical data set 212 of that second patient. Thus, analysis of the second patient's biochemical data set 212, given their diabetes stage/therapy of the patient 232 (that their biochemical data set 212 is impacted by the influence of two drugs they are currently taking, results in quite a different course of action (diabetes patient treatment guidance 308) for the second patient than the first patient even if they have similar marker values in their respective biochemical data sets 212. As such, the biochemical data set 212 of the first and second patient is interpreted differently. That is, the diabetes patient treatment guidance is going to try to move the values of the markers in the patient's biochemical data set 212 differently with the intervention (diabetes patient treatment guidance 308) and thus move the underlying pattern function differently for these two patients.

In this regard, the demonstration of the magnitude of various forms of intervention on fasting glucose levels, the OGTT test, HbA1C levels, proinsulin levels, C-peptide levels, insulin levels, adiponectin levels, and hs-CRP levels illustrated in FIGS. 6 and 7, in response to various forms of intervention, is drawn for a patient that has not yet undergone drug treatment. The effect of each drug class on the markers will be different for those patients that have undergone some form of treatment. Accordingly, different decision rules, with firing conditions and different diabetes treatment guidance to match such patients are drawn than the decision rules that are drawn to pre-administration baseline patients. The effects of each drug will have a difference in magnitude for post-administration patients than illustrated in FIGS. 6 and 7. However, the responses will not be directionally different. That is, an effect of a drug would not change from being beneficial for a marker to being adverse for a marker, but there would be significant differences in the magnitude of the impact on the marker.

In FIGS. 6 and 7, a first marker represented by a larger arrow undergoes a stronger effect than a second marker represented by a smaller arrow with the proviso that the effect on both markers will deviate in magnitude depending on the starting treatment condition of the patient. In fact, there are substantial differences in the impact of a marker value that can be realized depending on their current treatment condition/diabetes stage 232. For example, consider the case of a patient already on insulin and three drugs total, meaning they are taking two additional medicines beyond insulin. The patient may have very little β-cell function left at all at that point. β-cell are unique cells in the pancreas that produce, store and release the hormone insulin. So even if a drug was prescribed to affect the β-cells as much as we possible, there is just not much response left and so the directional change associated with the drug for the β-cells remains consistent with a pre-administration baseline, but the magnitude will be much smaller than that of the pre-administration baseline/pre-diabetes or early stage diabetes patient. On the other hand, consider the case of someone who is on a single pill early in the disease where they have not even adequately addressed a particular pattern. Adding another drug for patients in this instance could have a really big effect, because there is a lot of latent capacity that is substantially not being used.

As such, the systems and methods of the present disclosure take quantitatively into account these changes in magnitude, depending on the stage of therapy on a category by category basis. That is, a deliberate attempt is made to not be overly precise about the exact marker numbers and more precise about multiple dimensions in the profile. In other words, more emphasis is placed on determining for a given patient when insulin resistance is simply "significant," or is "really severe," that is categorical classification into discrete ranges as a basis for establishing firing conditions 306, versus establishing first conditions as a function of a continuous range: e.g., trying to establish a firing condition as a function of whether a patient's proinsulin value is 14 versus, 14.5, versus 15.0 versus 16.

In typical instances, diabetes patient treatment guidance 308 identifies drug classes rather than specific drugs within a class. This allows a physician to choose a specific drug within a recommended drug class. It may be the physician has more experience with dosing one drug in the class than another. Moreover, the diabetes patient treatment guidance is agnostic to drugs within a given class in recognition of other factors as well, including the real world limitation today on formulary availability. For instance, often a particular brand is simply not available for a particular case, because of an administrative decision unrelated to the practice of medicine. For instance, certain companies' drugs being listed as preferred providers, some drugs not being covered by insurance companies because there is a generic equivalent, etc. In this way, the diabetes patient treatment guidance circumvents brand beliefs, the cumulative impact of marketing, prescribing physician's beliefs about particular drugs in a class, etc. By limiting diabetes patient treatment guidance to the drug class level, as opposed to recommending certain drugs within a class over drugs in the same class, what the systems and methods of the present disclosure provide, using an analogy to cars, is information about what drug class is a sports car, what drug class is a station wagon, what drug class is a pickup truck. If the systems and methods of the present disclosure were to try to provide diabetes patient treatment guidance that discriminates between drugs in the same drug class, again using the analogy to cars, this would be arguing at the level that a Chrysler pickup is better than a Ford pickup which is better than a GM pickup, which is a situation to be avoided because it is subjective in view of the lack of suitable clinical trials to prove such relationships and because of non-medical policies that affect formulation availability.

In this way, further, the systems and methods of the present disclosure focus on major decisions, such as whether to treat the β-cells or not. That is, to identify which treatment objectives are major objectives, which treatment objectives are minor, and which treatment objectives will not even be addressed at all in the diabetes patient treatment guidance of a given patient.

Block 418.

Figure 9:
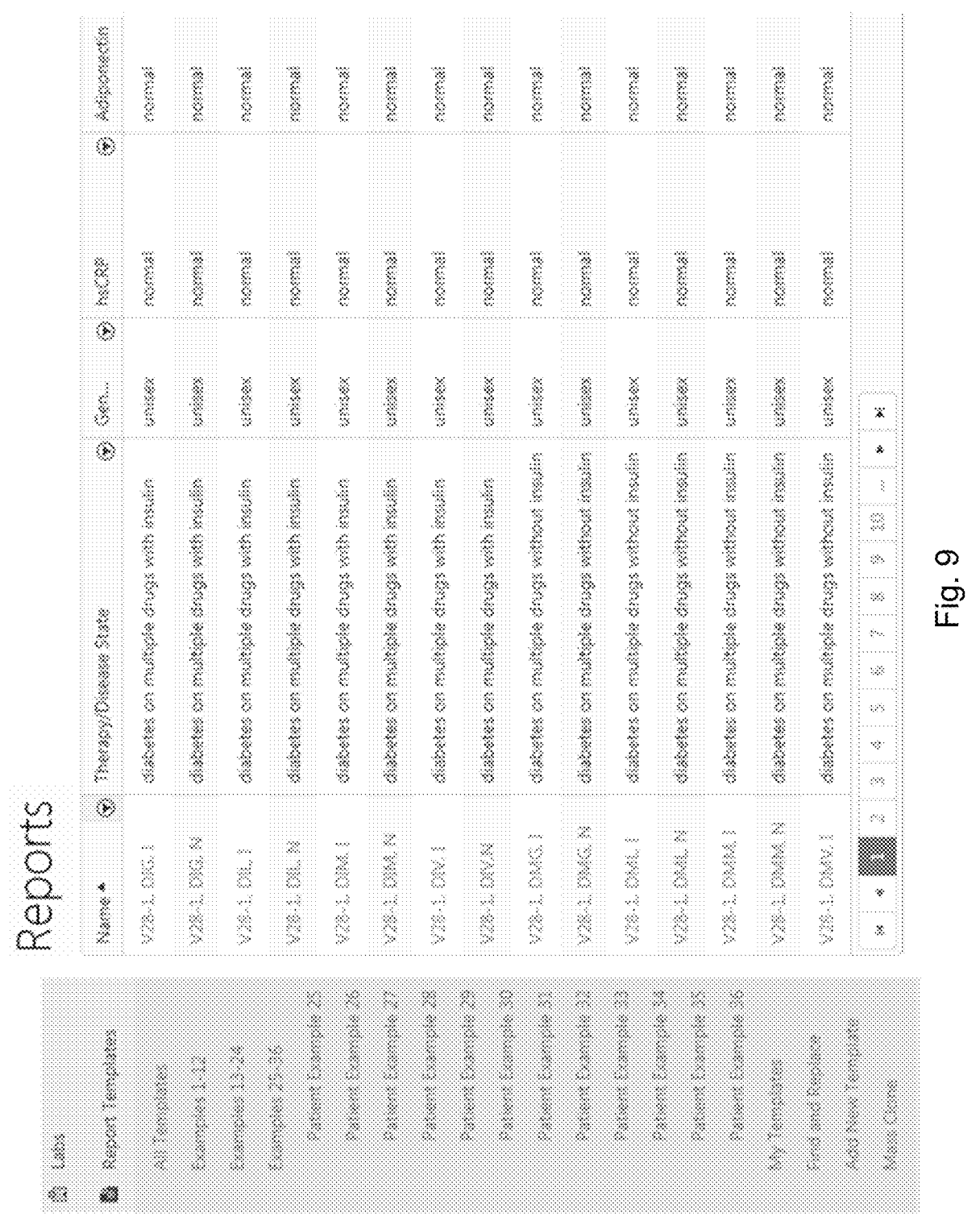

Referring to block 418 of FIG. 4, the method further includes preparing a report based on an identity of the first patient pattern. An example of one such report is provided in FIGS. 10A through 10G for a particular patient that has diabetes and is presently taking multiple drugs without insulin. The report provides a rank ordering of intervention classes among a set of preferred intervention classes based on the identity of the first patient pattern. The report collectively illustrated across FIGS. 10A through 10G is one of a plurality of such reports listed in example FIG. 9, each for a different set of marker values, or more precisely, range of marker values in the biochemical data set 212 and demographic data set 228. Reports may vary over time in content, number of pages, amount of detail, and the like once they are in the market, depending on customer needs.

Each such report is a combination of assessments made using the systems and methods of the present disclosure as well as a summary of information relevant to the patient condition from the literature. The report allows a clinician to make real world determination such as the effect that will be realized for a given patient from a given drug class, and then based on such information, how this relates to the patient's profile (e.g., biochemical data set 212). The reports provide ample room for medical judgment in how the profile is weighted. For example, consider the case where the patient profile (e.g., biochemical data set 212) shows the patient has severe cardiovascular inflammation indicating a lot of risk for life-altering things like strokes, and a lot of insulin resistance. In such an instance the report may advise that the treating physician should really focus on those two things. Both of those are significant risk drivers over the course of the next few years of this person's life. An individual physician might decide for whatever reason they don't think that is important. That is why the report supplies as much detail as illustrated in FIGS. 10A through 10J. All the raw data of the tests (e.g., the biochemical data set 212 marker values and the demographic data set 228 marker values), and each drug class is considered. Sometimes, for good reason, sometimes not for good reason, probably, an individual clinician may disagree with some aspect of the report. However, even in such instances the individual clinician has enough information, in the report, to look at the situation and actively think about the questions—e.g., is drug class A better than drug class B better than drug class C for this individual patient (given their biochemical data set 212 marker values and the demographic data set 228 marker values), and are there reasons with this patient that maybe I would do something different? For instance, perhaps the patient already indicated that they are quite willing to start up significant cardiovascular treatment. Perhaps there is relevant family history information, such as the patient's uncle recently died of a stroke, etc., which causes a patient and their treating clinician to be more aggressive (or less aggressive) than recommended by the report. So in such a case, the doctor might then go off in a slightly different treatment direction for other aspects of the diabetes condition, beyond the cardiovascular condition, then recommended in the report, to compensate for the fact that they are already treating the cardiovascular condition more aggressively than recommended in the report. At the same time, there is sufficient information that the clinician can assess the trade-offs involved in taking a different course, rather than follow the order of those suggested by the report.

Figure 10A:
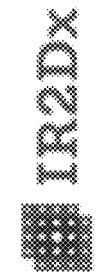
Figure 10E:
Figure 11:
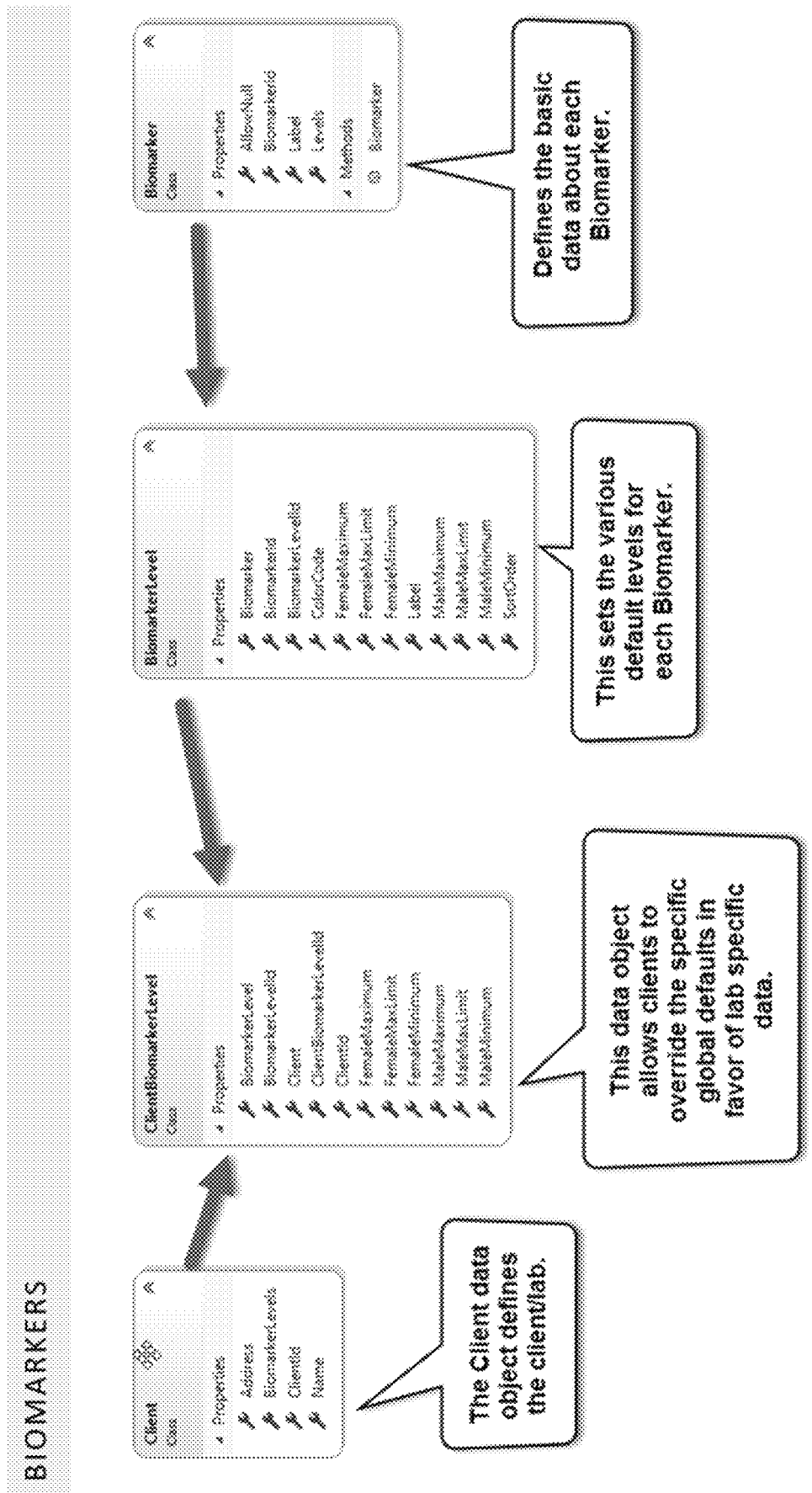
FIG. 11 illustrates a biomarker schema used to organize and process patient data in order to prepare a report that provides diabetes patient treatment guidance for a patient in accordance with an embodiment of the present disclosure.
Figure 12:
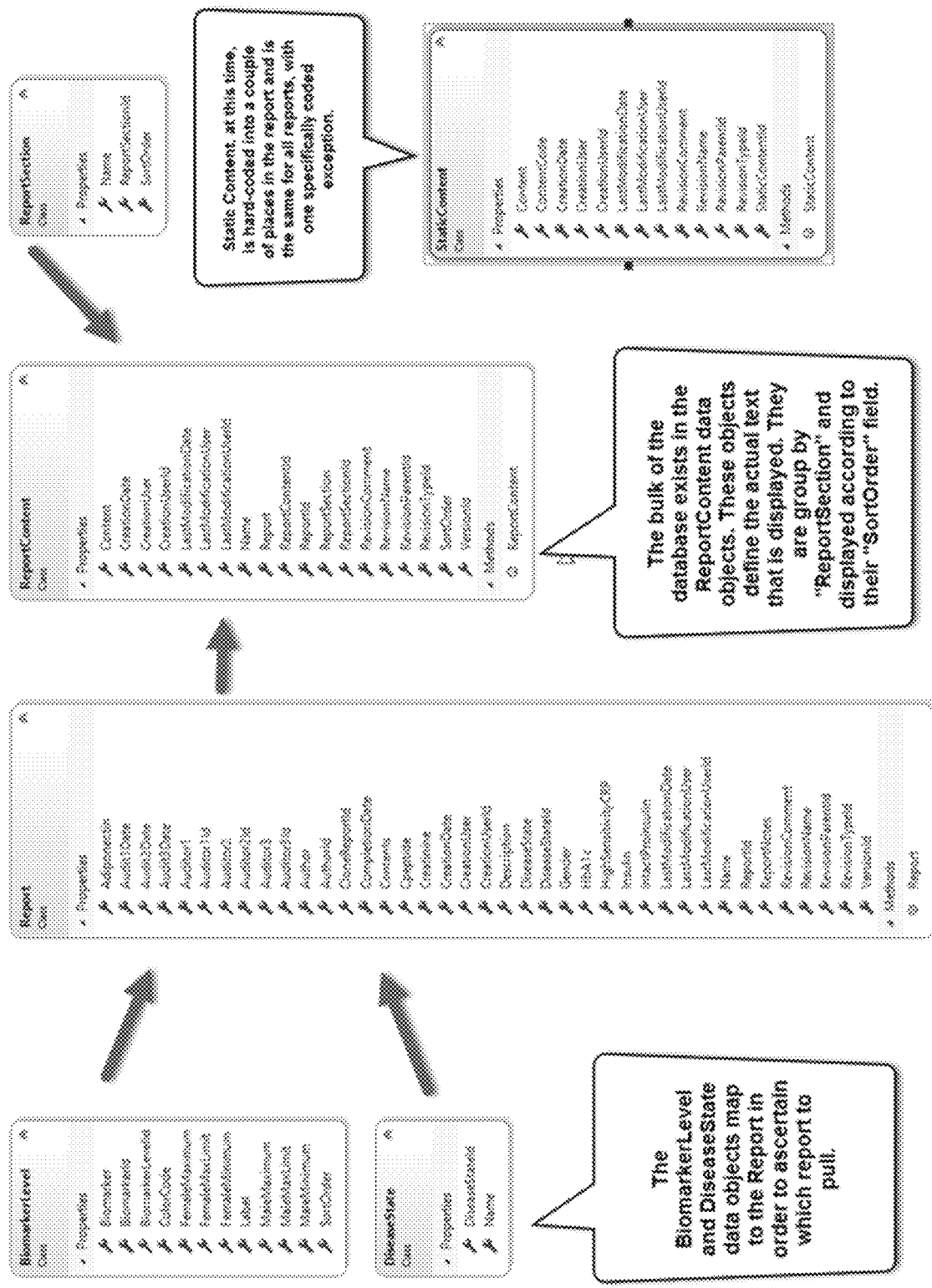
FIG. 12 illustrates a report content schema used to prepare a report that provides diabetes patient treatment guidance for a patient in accordance with an embodiment of the present disclosure.
Figure 13:
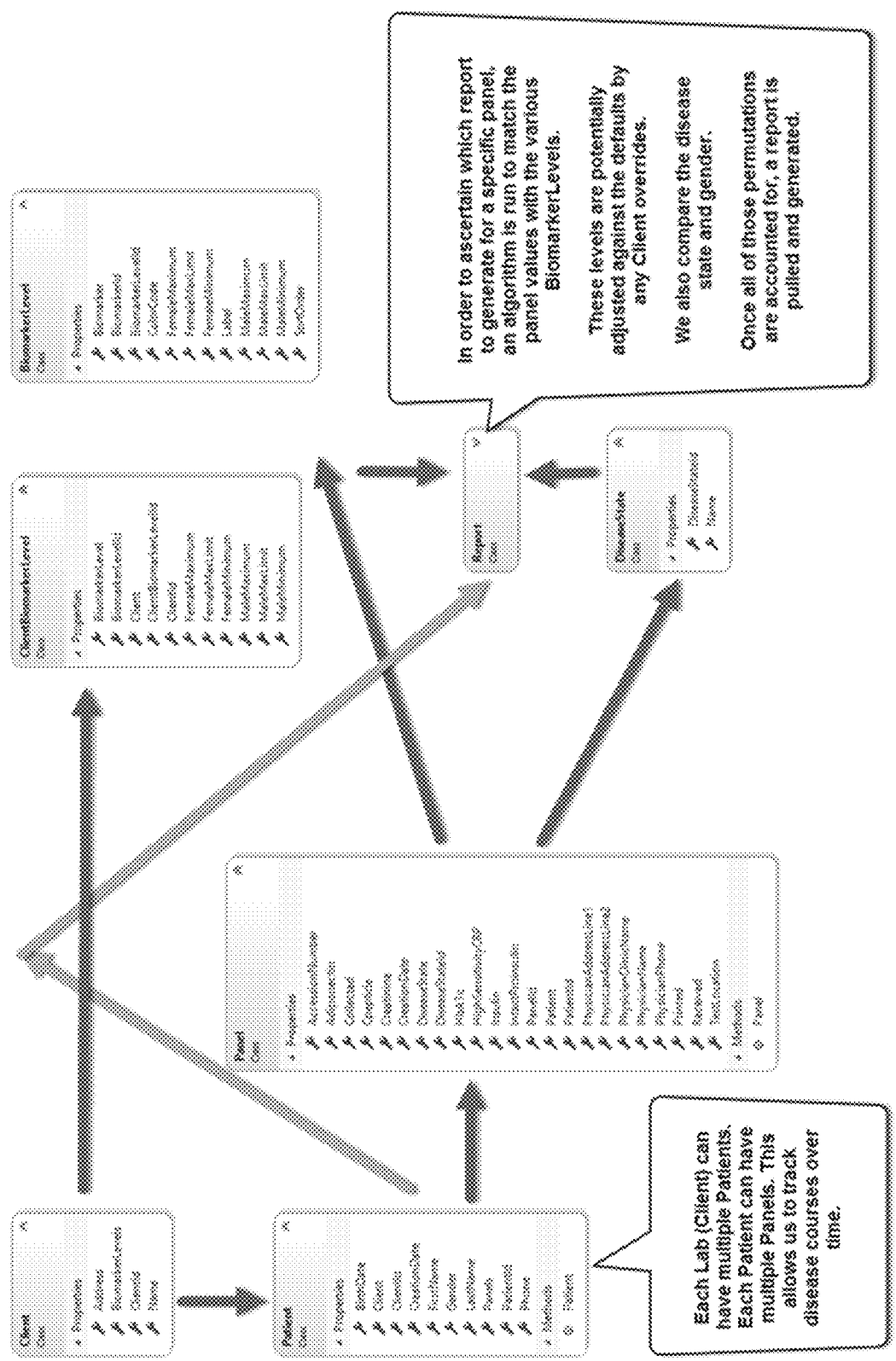
FIG. 13 illustrates a report content schema, in which each patient can have multiple panels in order to temporally track disease course, to prepare a report that provides diabetes patient treatment guidance for a patient in accordance with an embodiment of the present disclosure.

Referring to FIG. 10, an exemplary patient report is provided. In some embodiments, the patient report includes information for a medical practitioner (e.g., the patient reports of FIGS. 10A through 10J). In some embodiments, the patient report includes information for the patient (e.g., the patient reports of FIGS. 10K and 10L). In some embodiments, each patient report includes one or more sections. In some embodiments, a subset of the one or more sections is statically generated to include predetermined information, such as a predetermined set of biochemical data set values. In some embodiments, a subset of the one or more sections is generated from information stored in the one or more databases and/or modules of the diabetic patient care guidance device 250. In some embodiments, a subset of the one or more sections is one or more rules (e.g., decision rules 302 of FIG. 3), that if fired trigger particular information to be included in a respective section (e.g., a rule is fired if a patient has severe insulin resistance which provides a corresponding section on insulin resistance in the report).

Referring briefly to FIGS. 10A through 10J, a report that includes information for a medical practitioner is depicted. In some embodiments, the one or more sections include a patient panel test result section that includes information related to particular test results and/or biochemical data set values of the patient. For instance, referring briefly to FIG. 10A, a patient panel test result section for a medical practitioner is depicted. In some embodiments, the one or more sections include a test result interpretation section that includes information related to interpreting the results of the patient panel test and/or other auxiliary information inferred from test results and/or biochemical data set values. In some embodiments, the one or more sections include a current drug recommendations section that provides one or more treatment recommendations. In some embodiments, the one or more sections include a patient current condition section that includes information related to a patient's current stage and progression related to one or more medical conditions. In some embodiments, the one or more sections include a patient goal section that includes information related to one or more goals of the patient, including personal patient goals and/or biochemical data set value goals. In some embodiments, the one or more sections include a physician course of action section that includes information related to aiding an expert physician in determining a treatment guidance plan. In some embodiments, the one or more sections include a detailed drug recommendation section that includes information related to one or more specific drugs and/or drug classes including a prioritization thereof. In some embodiments, the one or more sections include a treatment guidance adjustment section that provides recommended adjustments for a medical condition and/or treatment guidance plan. In some embodiments, the one or more sections include a reference section that includes one or more cited references used in forming the respective report.

Referring briefly to FIGS. 10K and 10L, a report that includes information for a patient is depicted. In some embodiments, the report includes information related to the one or more above describe sections that is subsumed in a single section. This single section includes information that is not difficult for an uneducated patient to consume, such as an interpretation of one or more test results and/or biochemical data set values specifically for the patient.

Figure 14:
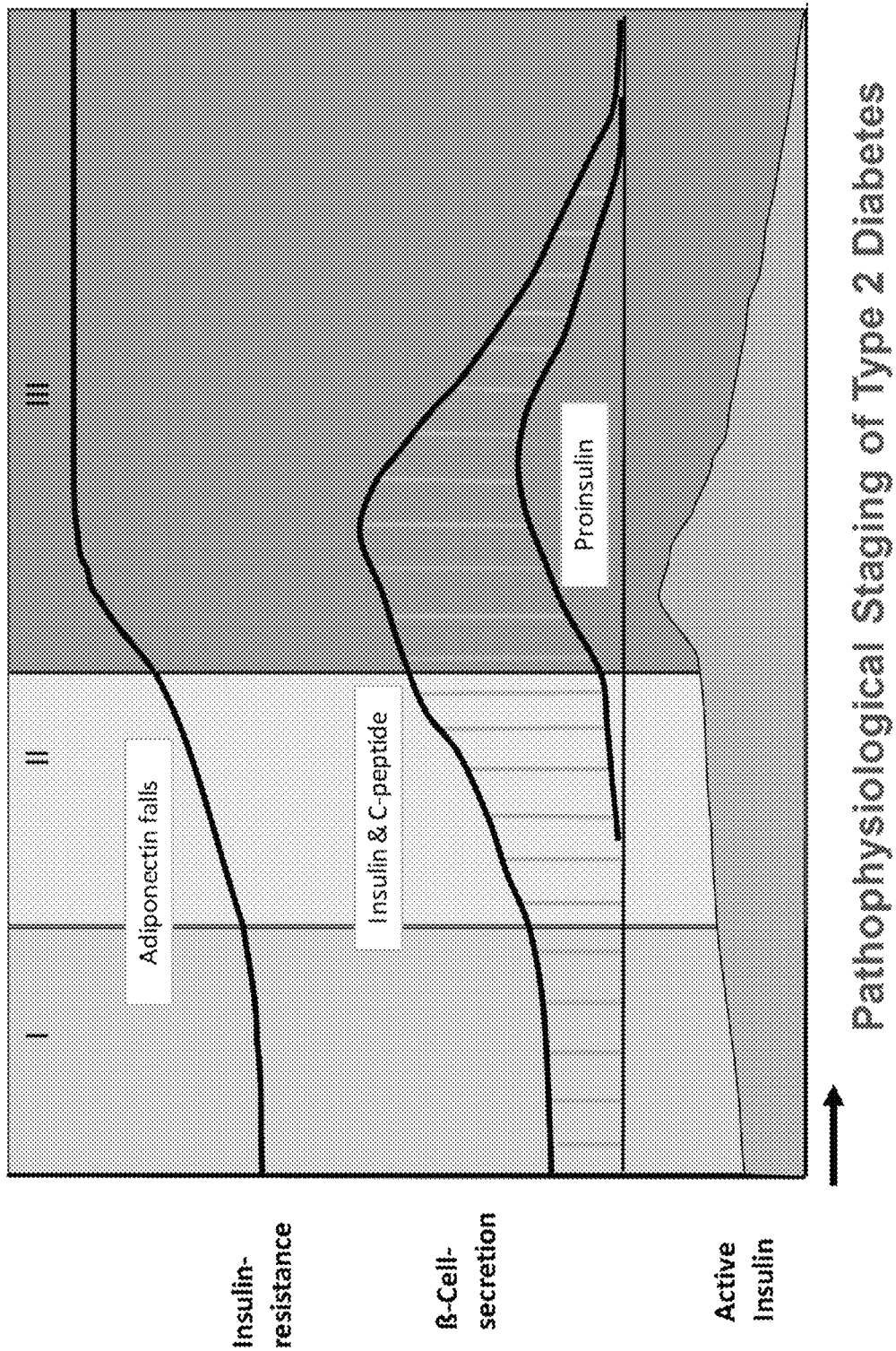
FIG. 14 illustrates a graphical representation of diabetes staging in relation to one or more patient conditions including insulin resistance, beta-cell secretion, and active insulin, in accordance with an embodiment of the present disclosure.

Referring to FIG. 14, in some embodiments, the report provides a graphic representation of one or more markers of a patient in relation to anticipated values for their stage of diabetes. This representation is useful as often an analysis of only numerical values can lead to misdiagnosis. For instance, as illustrated in FIG. 14, values for beta-cell secretion are within a common range for stage I and stage II of type 2 diabetes. Without including the insulin resistance values in the graphical representation, a physical would have difficulty determining which stage a patient is in, since many of the values alone provide inconclusive information.

As such there can be nuances on how the report is used. However, one objective of the systems and methods of the represent disclosure is that the report provided in accordance with block 418 have enough information that a clinician can make decisions that deviate from the diabetes patient treatment guidance 308. This is in recognition that there are subtleties in judgment made by the physicians when taking into account the entire profile (biochemical data set 212 and demographic dataset 228) in developing the disclosed decision rules 304 that, when looked at by someone else, may indicate a reason(s) to deviate. Moreover, the treating physician has to contend with real world obstacles rather than the abstract, such as when the best drug would be an injection, and the patient refuses injections, and the like. In such situation, these real world obstacles necessitate the treating physician to make an adjustment to the diabetes patient treatment guidance in the report 308, and once they make one such adjustment, they may need to make other ancillary adjustments to the diabetes patient treatment guidance 308 in the report to compensate for the first adjustment. As such, these factors, that are at times of a non-medical nature (e.g., refusal to accept injections, etc.) and may be more related to patient preference, combined with the substantial information regarding the patient's condition, all coupled with the goal of seeking to address the major treatment decisions (e.g., which drug class to take as opposed to which drug within a class to take), may require adjustments to the recommended treatment regimens. A simple outline of the most important treatment goals given a patient profile enables a treating physician to adapt the report to a patient's specific needs, both medical and non-medical.

As such, an important strength of the disclosed systems methods is the reliance on treating physician judgment given that the diabetes condition arises from such a complex set of factors. In short, weighing all the factors, both medical and non-medical, that could potentially affect the decision rules would lend itself to too many dimensions. Rather, the disclosed systems and methods rely on, in preferred embodiments the disclosed seven biochemical analytes (markers 214, 216, 218, 220, 222, 224, and 226, plus the patient's gender 230 and diabetes stage/therapy stage of the patient 232 to construct a multi-dimensional profile of the condition of the patient in a clinical context, and at the same time cover a limited number of important dimensions relevant to treatment selection. Thus, a report may be provided as to major objectives, which coupled with the treating physician's clinical perspective results in a treatment plan in which no major objectives are missed and the best impact is realized for a given patient panel.

As such the report in accordance with block 418 is written to be a partial aid for the decision. As such, the report provides helpful advice even though some embodiments of the disclosed systems and methods does not take into account a whole array of factors, such as what medications the patient's formulary will permit, whether the patient has any insurance coverage issues, what medications the patient is willing to take, patient beliefs (e.g., refuses to take a certain drug because friend/relative took the same drug and had bad side effects, etc.). These factors are generally considered to be a part of the art of medicine, since they cannot be assessed quantitatively, and thus included in a report. The reports in accordance with block 418 are written at sufficiently high level that the treating physician can take into account these unaddressed factors while still making sure that the major treatment objectives outlined by the report are addressed or at least considered. As such, the report effectively brings the treating physician to the point where they have an appreciation of the present biochemistry of their patient and, given this present biochemistry, which treatment objectives should be pursued nor not pursued. The treating physician can then adapt the report to specific drugs in recommended drug classes, or make informed decisions in forming a treatment plan that deviates from the report in order to address the factors, such as patient preference, formulary availability, etc., that the report does not attempt, and arguably should not attempt, to address. Thus, this limited goal of the present disclosure is a substantial contribution in the treatment of the diabetes condition.

As the above disclosure indicates, the stage of therapy informs the clinician about what is failing in the patient, for example the β-cells, etc. As another example, there is a class of drugs called sulfonylureas and a percentage of patients can do pretty well on those depending on their β-cell function. If a patient retains a large β-cell population, e.g. their pancreas is very resilient, they can keep on favorably responding to the sulfonylureas for a long time. The β-cell function markers provide some insight into this resilience. For instance, if the markers for β-cell function remain good for a particular patient, then sulfonylurea treatment can continue. On the other hand, if someone is on that drug class and their β-cells are essentially exhausted, the markers in the biochemical data set 212 would indicate this, and there is no point in continuing the sulfonylurea treatment to stimulate β-cells to release insulin. In such instances, for sulfonylureas for such a patient, the report in accordance with block 414 would say "not recommended" because it is not going to have any beneficial impact on the patient's condition.

As such another aspect that the reports in accordance with block 418 provide is information not only about what drug classes to consider but also which ones to not even bother with or those drug classes that are intermediate in likely efficacy, and as such are possible treatments. For example, sometimes there can be reasons for such treatment, or to continue such treatment if it is already underway. For example, the patient may already be on a drug, there may be cost issues, that give rise to diabetes patient treatment guidance 308 to the effect that while a certain drug class that the patient is currently taking is not on the optimal list for the particular patient profile, but because they are already on it and they are used to it the diabetes patient treatment guidance 308 notes the advantage of continuing on with the drug (or drug class) at that point from just a simplistic compliance point of view. The patient is used to it. This would include a drug class that, if treatment were starting de novo, wouldn't have been prescribed to the patient. But since it has been prescribed, a report in accordance with block 418 may provide intermediate support for continuing use of the drug.

To be clear, in preferred embodiments of the systems and methods of the present disclosure, specific drugs that the patient is currently taking are not provided as part of the demographic data set 228. Rather, in some embodiments, the diabetes stage/therapy stage of the patient requires that each patient be classified into one of five categories, either they are (i) diagnosed as pre-diabetes, (ii) diagnosed with diabetes but not taking a drug (e.g., they may have a fairly mild case where the doctor prescribed exercise and diet changes, for a period of time such as a year, and it didn't really work and so that patient has a diabetes diagnoses but no drug yet), (iii) the patient has been prescribed a first line drug meaning that the patient is on one drug, (iv) the patient has prescribed multiple drugs without insulin and (v) the patient has been prescribed multiple drugs with insulin. Such embodiments of the present disclosure do not discriminate between situations in which a patient is taking two or three kinds of diabetes drugs because it doesn't make a lot of difference. The real differentiator is whether the patient is taking insulin because that is a direct effect to basically replace the pancreatic production of insulin. As such, there are quite a few cases where the situation of the patient's disease state in therapy 232 combined with the marker data in the biochemical data set 212 will lead down a path to say that a particular drug class is not recommended for a given patient or that it is possible that there are others drug classes that are better.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a non-transitory computer readable storage medium. For instance, the computer program product could contain the program modules shown in any combination of FIGS. 1, 2, 3, 5 and/or described in FIG. 4. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method for providing patient treatment guidance for a patient that is being tested or has been tested for a diabetic or pre-diabetic condition, the method comprising:
   obtaining a biochemical data set, via a computer system having a processor programmed to obtain the biochemical dataset, wherein the biochemical data set comprises a plurality of test results from a single blood draw of the patient, wherein the plurality of test results comprises at least three measurements from the group consisting of a high-sensitivity c-reactive protein test, an adiponectin level test, a proinsulin level test, an insulin level test, a C-peptide test, a HbA1c test, and an eGFR level test;

obtaining a demographic data set for the patient, via a computer system having a processor programmed to obtain the biochemical dataset, wherein the demographic data set comprises (i) an indication of a gender of the patient and (ii) an enumerated indication of a patient's stage of disease or a current therapy, wherein the enumerated indication of the patient's stage of disease or the current therapy is one of (a) diagnosed as pre-diabetes, (b) diagnosed with diabetes but not taking a drug (c) diagnosed with diabetes and taking a first line diabetes drug (d) diagnosed with diabetes and prescribed multiple diabetes drugs without insulin and (e) diagnosed with diabetes and prescribed multiple diabetes drugs with insulin, or (f) a current therapy for the diabetic or pre-diabetic condition;

selecting a subset of a plurality of decision rules from a plurality of decision rules based upon the biochemical data set and the demographic data set for the patient via a computer system having a processor programmed to perform the selecting;

running all or a portion of the biochemical data set and the demographic data set against the subset of decision rules via a computer system having a processor programmed to perform the running, wherein, in accordance with a determination that one or more firing conditions of each respective decision rule in the subset of decision rules is fired, a patient pattern is selected, from among a set of at least 20,000 patient patterns, through the comparison of (i) the determination that one or more firing conditions of each respective decision rule in the subset of decision rules is fired to (ii) each patient pattern in the set of at least 20,000 patient patterns, wherein the patient pattern comprises a pattern of insulin resistance, β-cell stress level, and cardiovascular inflammation; and preparing a report based on an identity of the patient pattern, via a computer system having a processor programmed to perform the preparing, wherein the report provides a first prioritization of intervention classes in a first priority ordering of a plurality of intervention classes for the diabetic or pre-diabetic condition based on the identity of the patient pattern, wherein the plurality of intervention classes comprises one or more drug classes in the group consisting of a metformin class, a sodium-glucose cotransporter-2 inhibitor class, a glucagon-like peptide-1 receptor agonists class, a dipeptidyl peptidase-4 inhibitor class, an insulin class, a thiazolidinedione class, a glinides class, and a sulfonylureas class.

2. The method of claim 1, wherein the plurality of test results comprises three, four, five, six, or seven measurements from the group consisting of a high-sensitivity c-reactive protein test, an adiponectin level test, a proinsulin level test, an insulin level test, a C-peptide test, an HbA1c test, and an eGFR test.

3. The method of claim 1, wherein the plurality of test results consists of measurements from a high-sensitivity c-reactive protein test, an adiponectin level test, a proinsulin level test, an insulin level test, a C-peptide test, a n HbA1c test, and an eGFR test.

4. The method of claim 1, wherein the plurality of test results consists of measurements of eight, nine, ten, eleven, twelve, thirteen, fourteen, or fifteen measurements from a high-sensitivity c-reactive protein test, an adiponectin level test, a proinsulin level test, an insulin level test, a C-peptide test, an HbA1c test, an eGFR test, and one or more analytes that define a dimension of a patient metabolic condition including a brain analyte, a gut analyte, a beta cell analyte, a liver analyte, a kidney analyte, and a cardiovascular analyte.

5. The method of claim 1, wherein the prioritization of intervention class includes a prioritization of one or more drugs in a respective drug class.

6. The method of claim 1, wherein one or more decision rules in the plurality of decision rules is determined according to an analysis of the biochemical data set and the demographic data of each patient across a cohort population of patients conducted by a plurality of expert physicians.

7. The method of claim 1, wherein one or more decision rules in the plurality of decision rules is determined according to an analysis of at least a peer reviewed reference pertaining to a drug class for treatment of diabetes.

8. The method of claim 1, wherein the prioritization of intervention classes includes a prioritization of one or more drug classes, exercise, and diet.

9. The method of claim 1, wherein the report provides a magnitude of anticipated efficacy of the patient pattern with respect to one or more patient metabolic conditions identified by the biochemical data set.

10. The method of claim 1, wherein the report comprises a plurality of sections, wherein each section in the plurality of sections is classified as:
a static section that includes predetermined information,
a dynamic section that includes predetermined information as determined by one or more decision rules in the plurality of decision rules, or
a reference section that includes information provided from one or more databases that is accessible to the computer.

11. The method of claim 1, wherein each firing condition in the one or more firing conditions of a respective decision rule in the plurality of decision rules includes one or more conditions selected from the group consisting of a diabetes stage of the patient, a number of medications currently being taken by the patient, a dosage of a medication currently being taken by the patient, a type of medication currently being taken by the patient, a type of medication previously taken by the patient, and a patient metabolic condition.

12. The method of claim 11, wherein a firing condition in the one or more firing conditions of a decision rule in the plurality of decision rules includes the patient metabolic condition and wherein the patient metabolic condition is classified on a non-dimensional scale.

13. The method of claim 1, wherein the plurality of intervention classes further comprises (i) diet and (ii) exercise.

14. The method of claim 1, wherein the report further provides a second prioritization of intervention class in a second priority ordering of the plurality of intervention classes for the diabetic or pre-diabetic condition based on the identity of the patient pattern.

15. The method of claim 1, wherein the running of all or a portion of the biochemical data set and the demographic data set against the subset of decision rules comprises determining a level of β-cell stress in the patient.

* * * * *